United States Patent
Lubisch et al.

(10) Patent No.: US 6,414,157 B1
(45) Date of Patent: Jul. 2, 2002

(54) 3-SUBSTITUTED TETRAHYDROPYRIDOPYRIMIDINONE DERIVATIVES, METHOD FOR PRODUCING THE SAME, AND THEIR USE

(75) Inventors: Wilfried Lubisch, Mannheim; Uta Dullweber, Frankenthal; Dorothea Starck, Ludwigshafen; Gerd Steiner, Kirchheim; Alfred Bach, Heidelberg; Franz Emling, Ludwigshafen; Xavier Garcia-Ladona, Kandel; Hans-Jürgen Teschendorf, Dudenhofen; Karsten Wicke, Altrip, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/529,231

(22) Filed: Apr. 10, 2000

(30) Foreign Application Priority Data

Oct. 24, 1997 (DE) .......................... 197 47 063

(51) Int. Cl.⁷ ..................... C07D 471/00; H61K 31/519
(52) U.S. Cl. ....................... 546/262; 544/279
(58) Field of Search ...................... 544/279; 514/252.16

(56) References Cited

FOREIGN PATENT DOCUMENTS

JP 0827149 * 1/1996

OTHER PUBLICATIONS

Eur. J. of Med. Chem. Chimica Therapeutica, Bd. 32, N4. 7–8 1997, XP 00295654, F. Claudi et al.

* cited by examiner

Primary Examiner—Mukund J. Shah
Assistant Examiner—Hong Liu
(74) Attorney, Agent, or Firm—Keil & Weinkauf

(57) ABSTRACT

3-substituted tetrahydropyridopyrimidinone derivatives of the formula (I) wherein the radicals have the meanings given in the Description, to a method for producing said derivatives and, to their use for producing active ingredients for drugs.

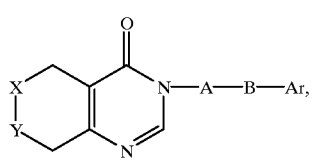

(I)

9 Claims, No Drawings

3-SUBSTITUTED TETRAHYDROPYRIDOPYRIMIDINONE DERIVATIVES, METHOD FOR PRODUCING THE SAME, AND THEIR USE

The invention relates to 3-substituted tetrahydropyrido-pyrimidinone derivatives, their preparation and use for producing active ingredients for drugs.

Classical antidepressants and the newer selective serotonin reuptake inhibitors (SSRIS) develop their antidepressant effect inter alia by inhibiting active reuptake of the transmitter into the presynaptic nerve endings. Unfortunately, the antidepressant effect thereof does not have its onset until treatment has lasted at least 3 weeks, and, moreover, about 30% of patients are therapy-resistant.

Blockade of presynaptic serotonin autoreceptors increases, by abolishing negative coupling, the serotonin release and thus the current transmitter concentration in the synaptic cleft. This increase in the transmitter concentration is regarded as the principle of the antidepressant effect. This mechanism of action differs from previously known antidepressants which activate both the presynaptic and somatodendritic autoreceptors and therefore result in a delayed onset of action, only after desensitization of these autoreceptors. Direct autoreceptor blockade bypasses this effect.

The derivatives described in JP 08027149 and JP 04054181 are known.

According to current knowledge, the presynaptic serotonin autoreceptor is of the 5-$HT_{1B}$ subtype (Fink et al., Arch. Pharmacol. 352 (1995), 451). Selective blockade thereof by 5-$HT_{1B/D}$ antagonists increases the serotonin release in the brain: G. W. Price et al., Behavioural Brain Research 73 (1996), 79–82; P. H. Hutson et al., Neuropharmacology Vol. 34, No. 4 (1995), 383–392.

However, surprisingly, the selective 5-$HT_{1B}$ antagonist GR 127 935 reduces serotonin release in the cortex after systemic administration. One explanation might be stimulation of somatodendritic 5-$HT_{1A}$ receptors in the graphed region by the released serotonin, which inhibits the firing rate of serotonergic neurons and thus serotonin release (M. Skingle et al., Neuropharmacology Vol. 34 No. 4 (1995), 377–382, 393–402).

One strategy for bypassing the autoinhibitory effects in serotonergic areas of origin thus aims at blockade of presynaptic 5-$HT_{1B}$ receptors. This hypothesis is supported by the observation that the effect of paroxetine on serotonin release in the dorsal raphe nucleus of the rat is potentiated by the 5-$HT_{1B}$ receptor antagonist GR 127 935 (Davidson and Stamford, Neuroscience Letts., 188 (1995), 41).

The second strategy includes blockade of both types of autoreceptors, namely the 5-$HT_{1A}$ receptors, in order to intensify neuronal firing, and the 5-$HT_{1B}$ receptors, in order to increase terminal serotonin release (Starkey and Skingle, Neuropharmacology 33 (3–4) (1994), 393).

5-$HT_{1B/D}$ antagonists, alone or coupled to a 5-$HT_{1A}$ receptor antagonistic component, should therefore cause a greater increase in serotonin release in the brain and might therefore be associated with advantages in the therapy of depressions and related psychological disorders.

It has now been found that 3-substituted tetrahydropyrido-pyrimidinone derivatives of the formula I

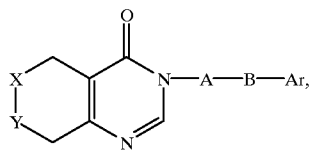

(I)

where
one of the two radicals X and Y is $CH_2$ and the other is $NR^1$, $R^1$ is hydrogen, ($C_{1-6}$) alkyl branched or unbranched, CO—($C_{1-4}$)-alkyl, $CO_2tBu$, CO-aryl and a phenylalkyl-$C_1$–$C_4$ radical which in turn may be substituted on the aromatic system by F, Cl, Br, I, $C_1$–$C_4$ alkyl, $C_1$–$C_4$ alkoxy, trifluoromethyl, hydroxyl, amino, cyano or nitro, A is branched or unbranched ($C_{1-10}$)-alkylene or straight-chain or branched ($C_{2-10}$)-alkylene which comprises at least one group Z which is selected from 0, S, $NR^2$, cyclopropyl, CHOH, a double or triple bond, $R^2$ is hydrogen and $C_1$–$C_4$ alkyl, B is 4-piperidine, 4-tetrahydro-1,2,3,6 pyridine, 4-piperazine or the corresponding cyclic compounds enlarged by one methylene group, with the linkage to A being via an N atom of B, and Ar is phenyl which is unsubstituted or substituted by ($C_{1-6}$) alkyl branched or unbranched, O—($C_{1-6}$) alkyl branched or unbranched, OH, F, Cl, Br, I, trifluoromethyl, $NR^2{}_2$, $CO_2R^2$, cyano or phenyl, or is tetralin, indan, fused aromatic systems such as naphthalene which is unsubstituted or substituted by ($C_{1-4}$)-alkyl or O($C_{1-4}$)-alkyl, anthracene or 5- or 6-membered aromatic heterocycles having 1 or 2 heteroatoms which are selected, independently of one another, from O and N, which may be fused to other aromatic radicals, and their salts with physiologically tolerated acids, have valuable pharmacological properties.

Particularly preferred compounds are those where
one of the two radicals X and Y is $CH_2$ and the other is $NR^1$, $R^1$ is hydrogen, ($C_{1-4}$)-alkyl branched or unbranched, CO—($C_{1-4}$)-alkyl, $CO_2tBu$, COPh or a phenylalkyl $C_1$–$C_2$ radical which in turn can be substituted on the aromatic system by F, Cl, Br, I, $C_1$–$C_4$ alkyl, $C_1$–$C_4$ alkoxy, trifluoromethyl, hydroxyl or cyano, A is ($C_{2-5}$) alkylene branched or unbranched or ($C_{2-5}$)-alkylene which comprises a group Z which is selected from CHOH, cyclopropyl, a double or a triple bond, B is 4-piperidine, 4-tetrahydro-1,2,3,6 pyridine, 4-piperazine or homopiperazine, where the linkage to A takes place via an N atom of B, and Ar is phenyl which is unsubstituted or substituted by ($C_{1-6}$)-alkyl branched or unbranched, O—($C_{1,6}$)-alkyl branched or unbranched, F, Cl, Br, I, trifluoromethyl, $CO_2R^2$, $NR^2{}_2$, cyano or phenyl, or is tetralin, indan, fused aromatic systems such as naphthalene which is unsubstituted or substituted by ($C_{1-4}$) alkyl or O($C_{1-4}$) alkyl, or 5- or 6-membered aromatic heterocycles having 1 or 2 nitrogen atoms, which may be fused to other aromatic radicals.

Particularly preferred compounds of the formula I are those listed in claim 3.

The compounds of the formula I may have one or more centers of asymmetry. The invention therefore includes not only the racemates but also the relevant enantiomers and diastereomers. The invention also includes the respective tautomeric forms.

The novel compounds of the formula I can be prepared by reacting a compound of the formula II

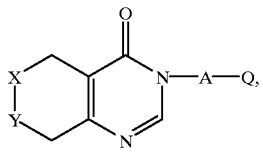 (II)

where A, X and Y have the abovementioned meanings, and Q is a group which can be eliminated (eg. Cl, Br, I, alkanesulfonyloxy or arylsulfonyloxy), with a compound of the formula III,

 (III), where B and Ar have the abovementioned meanings, in a manner known per se, and converting the compound obtained in this way where appropriate into the addition salt with a physiologically tolerated acid. It is likewise possible to react a compound of the formula IV

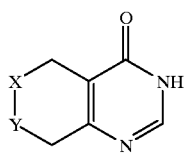 (IV)

with a compound of the formula V

 (V)

in a manner known per se.

Another variant of the synthesis comprises linking a compound of the formula VI

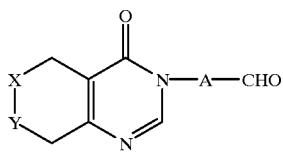 (VI)

with a compound of the formula III by a reductive amination known per se.

Compounds of the formula III can be synthesized by

1. Linking compounds of the formula VII

 (VII)

where $B^1$ is piperazine or homopiperazine and W is hydrogen or one of the usual amino protective groups (eg. Boc or Cbz), with a compound of the formula VIII

 (VIII), where P is $B(OH)_2$, $SnR_3$, OTf, Br, Cl, or I, and R is $C_1$–$C_4$-alkyl, in a known manner; or 2. linking compounds of the formula IX

 (IX), where $B^2$ is 4-tetrahydro-1,2,3,6-pyridine and the corresponding cyclic compounds enlarged by one methylene group, and $P^1$ is Cl, Br, I, $SnR_3$, where R is $C_1$–$C_4$-alkyl, or OTf, with a compound of the formula X

 (X), where W, P and Ar each have the abovementioned meanings, and the reactions take place by known processes as described, for example, in S. L. Buchwald et al. *J. Am. Chem. Soc.* 1996, 118, 7215,
J. F. Hartwig et al. *Tetrahedron Lett.* 1995, 36, 3604
J. K. Stille et al. *Angew. Chem.* 1986, 98, 504,
S. L. Buchwald et al. *Angew. Chem.* 1995, 107, 1456 or
J. F. Hartwig et al. *J. Am. Chem. Soc* 1996, 118, 7217 or
J. F. Hartwig et al. *J. Org. Chem.* 1997, 62, 1268,
S. L. Buchwald et al. *J. Org. Chem.* 1997, 62, 1264 and the literature cited therein or
S. L. Buchwald et al *J. Am. Chem. Soc* 1997, 119, 6054,
J. K. Stille, *Angew. Chem.* 1986, 98, 504 or
J. K. Stille et al. *J.Org. Chem.* 1990, 55, 3014,
M. Pereyre et al. "Tin in Organic Synthesis", Butterworth 1987; or 3. reducing compounds of the formula (XI)

 (XI), where $B^2$ has the abovementioned meaning, to compounds of the formula XII

 (XII), where $B^3$ is piperidines linked in the 1,4 positions, and the corresponding ring compounds enlarged by one methylene group; or 4. cyclizing compounds of the formula XIII

 (XIII), where W and Q have the meanings described above, with a compound of the formula XIV

 (XIV), where Ar has the abovementioned meaning, to give compounds of the formula XV

 (XV).

The substances of the formulae III and V which are required as starting materials for synthesizing the novel compounds are known or can be synthesized by known processes (eg. *Organikum* Barth Dt. Verl. der Wiss. 1993 or A. R. Katritzky, C. W. Rees (ed.) *Comprehensive Heterocyclic Chemistry* Pergamon Press) from analogous precursors.

Further reaction of the compounds

 (III)

prepared as in 1. to 4., with subsequent elimination of any protective groups, to give compounds of the formula V takes place by linkage with compounds of the formula XVI

Q—A—Q' (XVI), where Q and Q' are leaving groups, under conditions known per se.

The substances of the formula II, IV, VI and of the formula P—Ar, $NH_2$—Ar, W—$B^1$ and W—$B^2$—$P^1$ required as starting materials for synthesizing the novel compounds are known or can be synthesized from similar precursors by methods described in the literature (eg. B. Dumaitre, N. Dodic *J. Med. Chem.* 1996, 39, 1635 or A. Yokoo et al. *Bull. Chem. Soc. Jpn.* 1956, 29, 631 or L. Börjeson et al. *Acta Chem. Chem.* [sic] 1991, 45, 621 or *Organikum* Barth Dt. Verl. der Wiss. 1993 or A. R. Katritzky, C. W. Rees (ed.) *Comprehensive Heterocyclic Chemistry* Pergamon Press or *The Chemistry of Heterocyclic Compounds* J. Wiley & Sons Inc. NY and the literature cited in each of these).

The reactions described above generally take place in an inert organic solvent, eg. dimethylformamide, acetonitrile, dichloromethane, dimethyl sulfoxide, dimethoxyethane, toluene, ethyl acetate, xylene, a ketone such as acetone or methyl ethyl ketone, an alcohol such as ethanol or n-butanol, or a cyclic saturated ether, eg. tetrahydrofuran or dioxane.

The reactions generally take place at from 20° C. to the boiling point of the solvent and are generally complete within 1 to 20 hours. If required, they take place in the presence of an acid-binding agent such as sodium or potassium carbonate, sodium methoxide, sodium ethoxide, sodium hydride, organometallic compounds (butyllithium, alkylmagnesium compounds), potassium t-butoxide, pyridine or triethylamine.

Where appropriate, the reactions take place with use of a catalyst such as transition metals and their complexes, eg. Pd-C, $Pd(PPh_3)_4$, $Pd(OAc)_2$, $Pd(P(oTol)_3)_4$, $Pd_2(dba)_3$ or $Ni(COD)_2$.

The crude product is isolated in a conventional way, for example by filtration, removal of the solvent by distillation or extraction from the reaction mixture.

The novel compounds of the formula I can be purified either by recrystallization from conventional organic solvent or by column chromatography.

Besides the 3-substituted tetrahydropyridopyrimidinone derivatives, the invention also comprises the acid addition salts of the compounds of the formula I with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Further acids which can be used are described in "Fortschritte der Arzneimittelforschung", Volume 10, pages 224 et seq., Birkhäuser Verlag, Basle and Stuttgart, 1966.

The acid addition salts are prepared in a conventional way by mixing the free base with the appropriate acid, where appropriate in solution in an organic solvent, eg. a lower alcohol such as methanol, ethanol or propanol, an ether such as methyl t-butyl ether, a ketone such as acetone or methyl ethyl ketone, or an ester such as ethyl acetate.

The invention accordingly also relates to a therapeutic composition which comprises a compound of the formula I or its pharmacologically suitable acid addition salt as active ingredient in addition to conventional carriers and diluents, and to the use of the novel compounds for controlling diseases.

The novel compounds can be administered orally or parenterally, intravenously or intramuscularly, in a conventional way.

The dosage depends on the age, condition and weight of the patient and on the mode of administration. As a rule, the daily dose of active ingredient is about 1–100 mg/kg of body weight on oral administration and 0.1–10 mg/kg of body weight on parenteral administration.

The novel compounds can be used in conventional solid or liquid pharmaceutical forms, eg. as uncoated or (film) coated tablets, capsules, powders, granules, suppositories, solutions, ointments, creams or sprays. These are produced in a conventional way. The active ingredients can for this purpose be processed with conventional pharmaceutical auxiliaries such as tablet binders, fillers, preservatives, tablet disintegrants, flow regulators, plasticizers, wetting agents, dispersants, emulsifiers, solvents, release-slowing agents, antioxidants and/or propellant gases (cf. H. Sucker et. al: Pharmazeutische Technologie, Thieme-Verlag, Stuttgart, 1978). The administration forms obtained in this way normally contain from 1 to 99% by weight of active ingredient.

The novel compounds have a high affinity for $5\text{-}HT_{1B}$, $5\text{-}HT_{1D}$ and $5\text{-}HT_{1A}$ serotonin receptors. Approximately the same degree of affinity, at least of the same order of magnitude, is shown for these receptors. In addition, some of the novel compounds show good inhibition of serotonin reuptake, a principle which is implemented in most antidepressants.

These compounds are suitable as drugs for treating pathological states in which the serotonin concentration is reduced and in which it is wished for therapeutic purposes to block specifically the activity of the presynaptic $5\text{-}HT_{1B}$, $5\text{-}HT_{1A}$, $5\text{-}HT_{1D}$ receptors without having a great effect on other receptors. An example of such a pathological state is depression.

The compounds of the present invention can also be of use for treating mood disturbances with a central nervous causation, such as seasonal affective disorders and dysthymia. These also include anxiety states such as generalized anxiety, panic attacks, sociophobia, obsessive-compulsive neuroses and post-traumatic stress symptoms, memory disturbances including dementia, amnesias and age-related loss of memory, and psychogenic eating disorders such as anorexia nervosa and bulimia nervosa.

The novel compounds can additionally be used to treat endocrine disorders such as hyperprolactinemia and to treat vasospasms (especially of the cerebral vessels), hypertension and gastrointestinal disorders associated with disturbances of motility and secretion. Another area of use comprises sexual disorders.

The following examples serve to illustrate the invention without restricting it.

EXAMPLE 1

3-[2-[4-(2-methoxyphenyl)-1-piperazinyl]ethyl]-5,6, 7,8-tetra-hydro-6-benzylpyrido[4,3-d]pyrimidin-4 (3H)-one Preparation of the starting materials a) 5,6,7,8-Tetrahydro-6-benzylpyrido[4,3-d]pyrimidin-4 (3H)-one 4.7 g of sodium were ,a little at a time, allowed to react in 250 ml of ethanol, and a suspension of 14.2 g (0.05 mol) of methyl N-benzyl-4-piperidone-3-carboxylate in ethanol was then added dropwise at 5–10° C. The mixture was stirred for 30 minutes, after which 6 g (0.075 mol) of formamidine hydrochloride were added slowly, and the reaction mixture was heated under reflux for 10 h. The solvent was removed under reduced pressure and the residue was taken up in 100 ml of water and adjusted to pH=6.5–7 with 2N hydrochloric acid, so that the product precipitated out. The crystals were filtered off with suction and dried in a vacuum drying cabinet, and 8 g (66%). Melting point 88°

C. 5,6,7,8-Tetrahydro-7-benzylpyrido[3,4-d] pyrimidin-4 (3H)-one (melting point 199° C.) and methyl 5,6,7,8-tetrahydropyrido[4,3-d] pyrimidin-4(3H)-one-6-carboxylate (melting point 160° C.) were obtained similarly.

b) 1-(2-methoxyphenyl)-4-(2-chloroeth-l-yl) piperazine

At room temperature, a solution of 19.2 g (0.1 mol) of o-methoxyphenylpiperazine and 13.8 g (0.1 mol) of potassium carbonate in 200 ml of DMF was initially charged and, after 30 min, 30 ml (0.36 mol) of 1-bromo-2-chloroethane were added. The mixture was stirred at room temperature for 2 h. The mixture was poured into ice-water then extracted with methyl tert-butyl ether, and the organic phases were washed with water, dried with sodium sulfate and subsequently concentrated. The residue was dissolved in ethyl acetate and the hydrochloride was precipitated out by addition of 30% strength isopropanol/HCl solution, filtered off with suction and dried at 40° C. in a vacuum drying oven. This gave 17 g (67%) of substance. Melting point 200° C.

1-(2-Methoxyphenyl)-4-(3-chloroprop-1-yl)piperazine (melting point 217° C., hydrochloride), 1-(3,4-methylphenyl)-4-(2-chloroeth-1-yl) piperazine (melting point 260° C., hydrochloride), 1-(2-pyrimidyl)-4-(2-chloroeth-1-yl) piperazine (melting point 270° C., hydrochloride), 1-(naphth-1-yl)-4-(3-chloroprop-1-yl) piperazine (melting point 217° C., hydrochloride), were obtained in a similar manner.

Two exemplary syntheses for preparing the piperazines are shown below. 1-Tetralin-5-yl-piperazine 14.7 g (0.1 mol) of 5-aminotetralin and 18 g (0.11 mol) of bis(β-chloroethyl)amine hydrochloride in 300 ml of n-butanol were refluxed for 48 h, 5.4 g of sodium carbonate were added after cooling and the mixture was once more refluxed for 20 h. The precipitate which was formed by cooling was filtered off with suction, and taken up in water and admixed with 2N sodium hydroxide solution. The aqueous phase was extracted with ethyl acetate, and the extract was washed with water, dried over sodium sulfate and concentrated under reduced pressure. In this manner, it is possible to isolate 0.7 g (50%) of the product as an oil.

4-Piperazin-1-ylisoquinoline 4.51 g (21.7 mmol) of 4-bromoisoquinoline, 4.65 g (25.0 mmol) of t-butyl piperazine-N-carboxylate, 0.1 g (0.11 mmol) of tris(dibenzylideneacetone) dipalladium, 0.11 g (0.18 mmol) of 2,2'-bis(diphenylphosphino)-1,1'-dinaphthyl and 2.92 g (30.4 mmol) of sodium t-butoxide were admixed in 50 ml of toluene and stirred at 75° C. for 2 h. The reaction mixture was poured onto ice/sodium chloride and extracted with ethyl acetate, the organic phase was dried over sodium sulfate and the solvent was removed using a rotary evaporator. The product crystallized out, and it was filtered off with suction and washed with pentane. This gave 5.5 g (81%) of the Boc-protected piperazine (melting point 111° C.). 5.2 g (16.6 mmol) of this substance were taken up in 17 ml of dichloromethane and, at 0° C., slowly admixed with 17 ml (0.22 mol) of trifluoroacetic acid. The mixture was stirred at 0° C. for 4 h, poured into ice-water and extracted with dichloromethane. The aqueous phase was filtered, made alkaline and extracted with dichloromethane. After drying over sodium sulfate and substantial removal of the solvent the residue was diluted with diethyl ether and the hydrochloride was precipitated out using ethereal hydrochloric acid. This gave 3.2 g (67%) of the product. (Melting point 293° C.).

The following compounds were prepared similarly to the two processes described: 1-naphth-1-ylazepane (85° C., hydrochloride), 1-naphth-1-ylmethylpiperazine (oil), 4-piperazin-1-yl-indane (oil), 1-naphth-1-ylpiperazine (82° C.), 4-piperazin-1-ylquinazoline (205° C., decomposition) and 4-piperazin-1-ylquinazoline (320° C., hydrochloride). Other derivatives were commercially available.

Preparation of the end product 2.9 g (10 mmol) of chloroethylpiperazine and 2.8 g (20 mmol) of potassium carbonate were added to a solution of 2.4 g (10 mmol) of tetrahydropyridopyrimidine in 40 ml of DMF. After reaction at 90° C. for two hours, and then poured onto ice-water and extracted with ethyl acetate. The organic phase was washed with saturated sodium chloride solution and dried over sodium sulfate, and the solvent was removed under reduced pressure. The oil that remained was taken up in acetone, and the hydrochloride was precipitated out using isopropanol/HCl. This gave 4 g (75%) of the product were obtained (melting point 205° C.).

NMR: $CDCl_3$ 8.0 (s, 1H), 7.4–7.2 (m, 5H), 7.1–6.8 (m, 4H), 4.0 (t, 2H), 3.8 (s, 3H, 3.7 (s, 2H), 3.5 (s, 2H), 3.1 (brd. s, 4H), 2.8–2.6 (m, 10H) ppm.

The following compounds were obtained in a similar way:

EXAMPLE 2

3-[2-[4-(2-methoxyphenyl)-1-piperazinyl]ethyl]-5,6,7,8-tetra-hydro-7-benzylpyrido[3,4-d]pyrimidin-4(3H)-one (melting point 181° C., hydrochloride).

EXAMPLE 3

3-[3-[4-(2-methoxyphenyl)-1-piperazinyl]propyl]-5,6,7,8-tetrahydro-6-benzylpyrido[4,3-d]pyrimidin-4(3H)-one (melting point 198° C., hydrochloride).

EXAMPLE 4

3-[3-[4-(2-methoxyphenyl)-1-piperazinyl]propyl-5,6,7,8-tetrahydro-7-benzylpyrido[3,4-d]pyrimidin-4(3H)-one (melting point 190° C., hydrochloride).

EXAMPLE 5

3-[3-[4-(2-methoxyphenyl)-1-piperazinyl]2-hydroxypropyl]-5,6,7,8-tetrahydro-6-benzylpyrido[4,3-d]pyrimidin-4-(3H)-one.

EXAMPLE 6 t-butyl 3-[4-naphth-1-yl)-1-piperazinyl]ethyl]-5,6,7,8-tetrahydropyrido[4,3-d]pyrimidin-4-(3H)-one-6-carboxylate (melting point 170° C., hydrochloride).

EXAMPLE 7

3-[2-[4-naphth-1-yl)-1-piperazinyl]ethyl]-5,6,7,8-tetrahydro-pyrido[4,3-d]pyrimidin-4-(3H)-one (melting point 268° C., hydrochloride).

EXAMPLE 8

3-[2-[4-(naphth-1-yl)-1-piperazinyl]ethyl]-5,6,7,8-tetrahydropyrido[4,3-d]pyrimidin-4-(3H)-one (melting point 272° C., hydrochloride).

EXAMPLE 9

3-[2-[4-(quinazolin-4-yl)-1-piperazinyl]ethyl]-5,6,7,8-tetra-hydro-6-benzylpyrido[4,3-d]pyrimidin-4-(3H)-one (melting point 258° C., hydrochloride).

EXAMPLE 10

3-[2-[4-naphth-1-yl)-1-piperazinyl]ethyl]-5,6,7,8-tetrahydro-6-benzylpyrido[4,3-d]pyrimidin-4(3H)-one (melting point 227° C., hydrochloride).

EXAMPLE 11

3-[2-[4-(naphth-1-yl)-tetrahydro-1,2,3,6-pyridin-1-yl]eth-1-yl]-5,6,7,8-tetrahydro-6-benzylpyrido[4,3-d]pyrimidin-4-(3H)-one (melting point 216° C., hydrochloride).

Synthesis of the starting materials a) N-Boc-4-(trifluoromethanesulfonyloxy)-1,2,3,6-tetrahydropyridine At −78° C., a solution of 13.2 g (0.13 mol) of diisopropylamine in 200 ml of THF was deprotonated using 100 mol of nBuLi (1.6M in hexane), and, after 30 minutes at this temperature, 20.0 g (0.1 mol) of N-Boc-piperid-4-one dissolved in 50 ml of THF were added dropwise. After a further three hours at −78° C., a solution of 39.3 g (0.11 mol) of N,N,-bistrifluoromethanesulfonylaniline in 50 ml of THF was added, and the mixture was allowed to warm to room temperature overnight. For work-up, the mixture was admixed with water and extracted with ether, the organic phases were washed with NaHCO$_3$ solution and water and dried over sodium sulfate, and the solvent was concentrated. The crude product was purified by flash chromatography (silica gel, mobile phase heptane/ethyl acetate=3/1).

Yield: 20.2 g (60% of theory) 1H-NMR:(270 MHz, CDCl$_3$)δ=1.4 (s, 9H); 2.4(m, 2H); 3.6 (t, 2H); 4.1 (m, 2H); 5.8 (m, 1H)ppm b) N-Boc-4-naph-1-yltetrahydro-1,2,3,6-pyridine 22 ml of 2M sodium carbonate solution, 7.63 g (44.4 mmol) of naphthyl-1-boronic acid, 4.13 g (97.6 mmol) of lithium chloride, 0.85 g (4.44 mmol) of copper(l) iodide and 2.1 g (1.77 mmol) of tetrakistriphenylphosphinepalladium were added successively to 14.7 g (44.4 mmol) of the compound described above dissolved in 115 ml of dimethoxyethane, and the mixture was boiled for 4 h. For work-up, aqueous ammonia solution was added and the mixture was extracted with water and ethyl acetate, the extract was dried over sodium sulfate and the residue which was obtained after evaporation of the solvent, was purified by flash chromatography (silica gel, mobile phase heptane/ethyl acetate=4/1).

Yield: 8.2 g (57% of theory) 1H-NMR (270 MHz, CDCl$_3$): δ=1.4 (s, 9H); 2.5 (m, 2H); 3.7(t, 2H); 4.1 (m, 2H); 5.8 (m, 1H); 7.2–7.5(m, 3H); 7.3–8.0 (m, 3H) ppm.

c) 4-Naphth-1-yltetrahydro-1,2,3,6-pyridine 7.84 g (25.3 mmol) of N-Boc-4-naphth-1-yltetrahydro-1,2,3,6-pyridine were stirred overnight at room temperature with 200 ml of ethereal hydrochloric acid, and the precipitated product was filtered off and dried.

Yield: 5.5 g (88% of theory).

d) Preparation of the end compound 0.51 g (2 mmol) of 4-maphth-1-yltetrahydro-1,2,3,6-pyridine dissolved in ml of dry DMF was admixed with 0.61 g (2 mmol) of 3-(2-chloroeth-l-yl)-3, 5,7,8-tetrehydro-4-oxo-6-benzylpyrido [4,3-d]pyrimidine and with 2 ml (17 mmol) of thiethylamine, and the mixture was stirred at 120° C. for 5 h. The organic phase was diluted with ether, washed with water and dried over sodium sulfate, and the solvent was removed under reduced pressure. The resulting crude product was purified chromatographically, giving a white solid by precipitating the salt using ethereal hydrochloric acid solution.

Yield: 0.2 g (20% of theory) Melting point: 237° C.

EXAMPLE 12

3-[2-[4-(Naphth-1-yl)piperidin-1-yl]eth-1-yl]-5,6,7,8-tetrahydro-6-benzylpyrido[4,3-d]pyrimidin-4-(3H)-one 4-Naphth-1-ylpiperidine 3.7 g (15.3 mmol) of 4-naphth-1-yltetrahydro-1,2,3,6-pyridine dissolved in methanol, were hydrogenated at room temperature with hydrogen for 48 h, with addition of 0.8 g of palladium on carbon. The catalyst was filtered off, and the solvent was concentrated.

Yield: 1.8 g (56% of theory) 1H-NMR (270 MHz, CDCl$_3$) δ=1.6–1.8 (m, 2H); 2.0 (m, 2H); 2.9 (dt, 2H); 3.3 (d, 2H; 3.5 (tt, 1H); 7.4–7.6 (m, 4H); 7.7 (d, 1H); 7.9 (d, 1H); 8.1 (d, 1H) ppm.

Preparation of the end product 0.42 g(2mmol) of 4-naphtha-1-ylpiperidine, dissolved in 30 ml of dry DMF, was admixed with 0.61 g (2 mmol) of 3-(2-chloroeth-1-yl)-3.5.7.8-tetrahidro-4-oxo-6-benzylpyrido [4,3d] pyrimidine and with 2 ml (17 mmol) of triethylamine, and the mixture was stirred at 120° C. for 5 h. The organic phase was diluted with ether, washed with water and dried over sodium sulfate, and the solvent was removed under reduced pressure. The resulting crude product was purified chromatographically, giving a white solid by precipitating the salt using ethereal hydrochloric acid solution.

Yield: 0.24 g (27% of theory) 1H-NMR (270 MHz, CDCl$_3$)δ=8.3 (s, 1H), 8.0 (d,1H), 7.8 (d, 1H), 7.7 (t, 1H), 7.5–7.2 (m, 9H), 4.5 (s, 2H), 4.0 (s, 2H), 3.7–2.3 (m, 15H), 2.1 (d, 2H) ppm.

Other preferred compounds of the formula I according to the invention are listed in the table below.

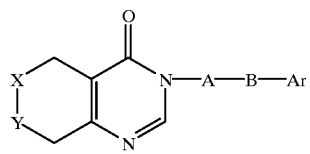

| No. | X | Y | R$^1$ | A | R$^2$ | B | Ar | M.p. hydrochloride |
|---|---|---|---|---|---|---|---|---|
| 13. | NR$^1$ | CH$_2$ | H | C$_2$ | | 1,4-piperazinylene | Ph | |
| 14. | NR$^1$ | CH$_2$ | H | C$_2$ | | 1,4-piperazinylene | 2-OH—Ph | |
| 15. | NR$^1$ | CH$_2$ | H | C$_2$ | | 1,4-piperazinylene | 2-OMe—Ph | |
| 16. | NR$^1$ | CH$_2$ | H | C$_2$ | | 1,4-piperazinylene | 2-Me—Ph | |
| 17. | NR$^1$ | CH$_2$ | H | C$_2$ | | 1,4-piperazinylene | 2-CN—Ph | |
| 18. | NR$^1$ | CH$_2$ | H | C$_2$ | | 1,4-piperazinylene | 2-Cl—Ph | |

-continued

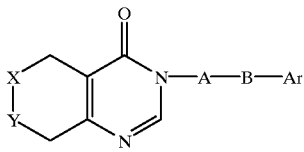

| No. | X | Y | R$^1$ | A | R$^2$ | B | Ar | M.p. hydro-chloride |
|---|---|---|---|---|---|---|---|---|
| 19. | NR$^1$ | CH$_2$ | H | C$_2$ | Me | 1,4-piperazinylene | 3-NR$^2{}_2$—Ph | |
| 20. | NR$^1$ | CH$_2$ | H | C$_2$ | Me | 1,4-piperazinylene | 3-CO$_2$R$^2$—Ph | |
| 21. | NR$^1$ | CH$_2$ | H | C$_2$ | | 1,4-piperazinylene | 3-CF$_3$—Ph | |
| 22. | NR$^1$ | CH$_2$ | H | C$_2$ | | 1,4-piperazinylene | 3-NO$_2$—Ph | |
| 23. | NR$^1$ | CH$_2$ | H | C$_2$ | | 1,4-piperazinylene | 3-F—Ph | |
| 24. | NR$^1$ | CH$_2$ | H | C$_2$ | | 1,4-piperazinylene | 4-iC$_3$—Ph | |
| 25. | NR$^1$ | CH$_2$ | H | C$_2$ | | 1,4-piperazinylene | 4-I—Ph | |
| 26. | NR$^1$ | CH$_2$ | H | C$_2$ | | 1,4-piperazinylene | 4-Br—Ph | |
| 27. | NR$^1$ | CH$_2$ | H | C$_2$ | | 1,4-piperazinylene | 4-O(n-C$_4$)—Ph | |
| 28. | NR$^1$ | CH$_2$ | H | C$_2$ | | 1,4-piperazinylene | 4-t-Bn—Ph | |
| 29. | NR$^1$ | CH$_2$ | H | C$_2$ | H | 1,4-piperazinylene | 4-CO$_2$R$^2$—Ph | |
| 30. | NR$^1$ | CH$_2$ | H | C$_2$ | n-C$_3$ | 1,4-piperazinylene | 4-NR$^2{}_2$—Ph | |
| 31. | NR$^1$ | CH$_2$ | H | C$_2$ | | 1,4-piperazinylene | 3-Me, 4-Me—Ph | |
| 32. | NR$^1$ | CH$_2$ | H | C$_2$ | | 1,4-piperazinylene | 2-Cl, 4-NO$_2$—Ph | |
| 33. | NR$^1$ | CH$_2$ | H | C$_2$ | | 1,4-piperazinylene | 3-tBu, 5-CF$_3$—Ph | |
| 34. | NR$^1$ | CH$_2$ | H | C$_2$ | | 1,4-piperazinylene | 2-OMe, 5-Ph—Ph | |
| 35. | NR$^1$ | CH$_2$ | H | C$_2$ | | 1,4-piperazinylene | 2-OMe, 5-Cl, 5-Me—Ph | |
| 36. | NR$^1$ | CH$_2$ | H | C$_2$ | | 1,4-piperazinylene | 5-tetralinyl | |
| 37. | NR$^1$ | CH$_2$ | H | C$_2$ | | 1,4-piperazinylene | 4-indanyl | |
| 38. | NR$^1$ | CH$_2$ | H | C$_2$ | | 1,4-piperazinylene | 1-naphthyl | |
| 39. | NR$^1$ | CH$_2$ | H | C$_2$ | | 1,4-piperazinylene | 2-OMe-1-naphthyl | |
| 40. | NR$^1$ | CH$_2$ | H | C$_2$ | | 1,4-piperazinylene | 2-Me-1-naphthyl | |
| 41. | NR$^1$ | CH$_2$ | H | C$_2$ | | 1,4-piperazinylene | 8-OMe-1-naphthyl | |
| 42. | NR$^1$ | CH$_2$ | H | C$_2$ | | 1,4-piperazinylene | 3-indolyl | |
| 43. | NR$^1$ | CH$_2$ | H | C$_2$ | | 1,4-piperazinylene | 2-quinazolinyl | |
| 44. | NR$^1$ | CH$_2$ | H | C$_2$ | | 1,4-piperazinylene | 4-quinazolinyl | |
| 45. | NR$^1$ | CH$_2$ | H | C$_2$ | | 1,4-piperazinylene | 2-quinoxalinyl | |
| 46. | NR$^1$ | CH$_2$ | H | C$_2$ | | 1,4-piperazinylene | 1-phthalazinyl | |
| 47. | NR$^1$ | CH$_2$ | H | C$_2$ | | 1,4-piperazinylene | 1-quinolinyl | |
| 48. | NR$^1$ | CH$_2$ | H | C$_2$ | | 1,4-piperazinylene | 1-isoquinolinyl | |
| 49. | NR$^1$ | CH$_2$ | H | C$_2$ | | 1,4-piperazinylene | 4-isoquinolinyl | |
| 50. | NR$^1$ | CH$_2$ | H | C$_2$ | | 1,4-piperazinylene | 7-benzofuranyl | |
| 51. | NR$^1$ | CH$_2$ | H | C$_2$ | | 1,4-piperazinylene | 2-pyrimidinyl | |
| 52. | NR$^1$ | CH$_2$ | H | C$_2$ | | 1,4-piperazinylene | 2-tBu, 4-CF$_3$-6-pyrimidinyl | |
| 53. | NR$^1$ | CH$_2$ | H | C$_2$ | | 1,4-piperazinylene | 2-pyridinyl | |
| 54. | NR$^1$ | CH$_2$ | H | C$_2$ | | 1,4-piperazinylene | 2-Ph-4-quinazolinyl | |
| 55. | NR$^1$ | CH$_2$ | H | C$_2$ | | 1,4-piperazinylene | 5-chromanyl | |
| 56. | NR$^1$ | CH$_2$ | H | C$_2$ | | 1,4-piperazinylene | 3-isoxazolyl | |
| 57. | NR$^1$ | CH$_2$ | H | C$_2$ | | 1,4-piperazinylene | 7-OMe-1-naphthyl | |
| 58. | NR$^1$ | CH$_2$ | H | C$_2$ | | 1,4-piperazinylene | 1-tetralinyl | |
| 59. | NR$^1$ | CH$_2$ | H | C$_2$ | | 1,4-piperazinylene | 2-Et-naphthyl | |
| 60. | NR$^1$ | CH$_2$ | H | C$_2$ | | 1,4-piperazinylene | 2-quinolinyl | |
| 61. | NR$^1$ | CH$_2$ | CH$_2$—Ph | C$_2$ | | 1,4-piperazinylene | Ph | |
| 62. | NR$^1$ | CH$_2$ | CH$_2$—Ph | C$_2$ | | 1,4-piperazinylene | 2-OH—Ph | |
| 63. | NR$^1$ | CH$_2$ | CH$_2$—Ph | C$_2$ | | 1,4-piperazinylene | 2-OMe—Ph | |
| 64. | NR$^1$ | CH$_2$ | CH$_2$—Ph | C$_2$ | | 1,4-piperazinylene | 2-Me—Ph | |
| 65. | NR$^1$ | CH$_2$ | CH$_2$—Ph | C$_2$ | | 1,4-piperazinylene | 2-CN—Ph | |
| 66. | NR$^1$ | CH$_2$ | CH$_2$—Ph | C$_2$ | | 1,4-piperazinylene | 2-Cl—Ph | |
| 67. | NR$^1$ | CH$_2$ | CH$_2$—Ph | C$_2$ | Me | 1,4-piperazinylene | 3-NR$^2{}_2$—Ph | |
| 68. | NR$^1$ | CH$_2$ | CH$_2$—Ph | C$_2$ | Me | 1,4-piperazinylene | 3-CO$_2$R$^2$—Ph | |
| 69. | NR$^1$ | CH$_2$ | CH$_2$—Ph | C$_2$ | | 1,4-piperazinylene | 3-CF$_3$—Ph | |
| 70. | NR$^1$ | CH$_2$ | CH$_2$—Ph | C$_2$ | | 1,4-piperazinylene | 3-NO$_2$—Ph | |
| 71. | NR$^1$ | CH$_2$ | CH$_2$—Ph | C$_2$ | | 1,4-piperazinylene | 3-F—Ph | |
| 72. | NR$^1$ | CH$_2$ | CH$_2$—Ph | C$_2$ | | 1,4-piperazinylene | 4-iC$_3$—Ph | |
| 73. | NR$^1$ | CH$_2$ | CH$_2$—Ph | C$_2$ | | 1,4-piperazinylene | 4-I—Ph | |
| 74. | NR$^1$ | CH$_2$ | CH$_2$—Ph | C$_2$ | | 1,4-piperazinylene | 4-Br—Ph | |
| 75. | NR$^1$ | CH$_2$ | CH$_2$—Ph | C$_2$ | | 1,4-piperazinylene | 4-O(n-C$_4$)—Ph | |
| 76. | NR$^1$ | CH$_2$ | CH$_2$—Ph | C$_2$ | | 1,4-piperazinylene | 4-tBu—Ph | |
| 77. | NR$^1$ | CH$_2$ | CH$_2$—Ph | C$_2$ | H | 1,4-piperazinylene | 4-CO$_2$R$^2$—Ph | |
| 78. | NR$^1$ | CH$_2$ | CH$_2$—Ph | C$_2$ | n-C$_3$ | 1,4-piperazinylene | 4-NR$^2{}_2$—Ph | |
| 79. | NR$^1$ | CH$_2$ | CH$_2$—Ph | C$_2$ | | 1,4-piperazinylene | 3-Me, 4-Me—Ph | |
| 80. | NR$^1$ | CH$_2$ | CH$_2$—Ph | C$_2$ | | 1,4-piperazinylene | 2-Cl, 4-NO$_2$—Ph | |
| 81. | NR$^1$ | CH$_2$ | CH$_2$—Ph | C$_2$ | | 1,4-piperazinylene | 3-tBu, 5-CF$_3$—Ph | |
| 82. | NR$^1$ | CH$_2$ | CH$_2$—Ph | C$_2$ | | 1,4-piperazinylene | 2-OMe, 5-Ph—Ph | |
| 83. | NR$^1$ | CH$_2$ | CH$_2$—Ph | C$_2$ | | 1,4-piperazinylene | 2-OMe, 4-Cl, 5-MePh | |

-continued

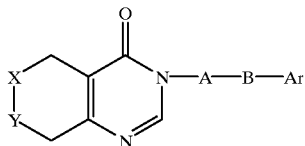

| No. | X | Y | R¹ | A | R² | B | Ar |
|---|---|---|---|---|---|---|---|
| 84. | NR¹ | $CH_2$ | $CH_2$—Ph | $C_2$ | | 1,4-piperazinylene | 5-tetralinyl |
| 85. | NR¹ | $CH_2$ | $CH_2$—Ph | $C_2$ | | 1,4-piperazinylene | 4-indanyl |
| 86. | NR¹ | $CH_2$ | $CH_2$—Ph | $C_2$ | | 1,4-piperazinylene | 1-naphthyl |
| 87. | NR¹ | $CH_2$ | $CH_2$—Ph | $C_2$ | | 1,4-piperazinylene | 2-OMe-1-naphthyl |
| 88. | NR¹ | $CH_2$ | $CH_2$—Ph | $C_2$ | | 1,4-piperazinylene | 2-Me-1-naphthyl |
| 89. | NR¹ | $CH_2$ | $CH_2$—Ph | $C_2$ | | 1,4-piperazinylene | 8-OMe-1-naphthyl |
| 90. | NR¹ | $CH_2$ | $CH_2$—Ph | $C_2$ | | 1,4-piperazinylene | 3-indolyl |
| 91. | NR¹ | $CH_2$ | $CH_2$—Ph | $C_2$ | | 1,4-piperazinylene | 2-quinazolinyl |
| 92. | NR¹ | $CH_2$ | $CH_2$—Ph | $C_2$ | | 1,4-piperazinylene | 4-quinazolinyl |
| 93. | NR¹ | $CH_2$ | $CH_2$—Ph | $C_2$ | | 1,4-piperazinylene | 2-quinoxalinyl |
| 94. | NR¹ | $CH_2$ | $CH_2$—Ph | $C_2$ | | 1,4-piperazinylene | 1-phthalazinyl |
| 95. | NR¹ | $CH_2$ | $CH_2$—Ph | $C_2$ | | 1,4-piperazinylene | 4-quinolinyl |
| 96. | NR¹ | $CH_2$ | $CH_2$—Ph | $C_2$ | | 1,4-piperazinylene | 1-isoquinolinyl |
| 97. | NR¹ | $CH_2$ | $CH_2$—Ph | $C_2$ | | 1,4-piperazinylene | 4-isoquinolinyl |
| 98. | NR¹ | $CH_2$ | $CH_2$—Ph | $C_2$ | | 1,4-piperazinylene | 7-benzofuranyl |
| 99. | NR¹ | $CH_2$ | $CH_2$—Ph | $C_2$ | | 1,4-piperazinylene | 2-pyrimidinyl |
| 100. | NR¹ | $CH_2$ | $CH_2$—Ph | $C_2$ | | 1,4-piperazinylene | 2-tBu, 4-$CF_3$-6-pyrimidinyl |
| 101. | NR¹ | $CH_2$ | $CH_2$—Ph | $C_2$ | | 1,4-piperazinylene | 2-pyridinyl |
| 102. | NR¹ | $CH_2$ | $CH_2$—Ph | $C_2$ | | 1,4-piperazinylene | 2-Ph-4-quinazolinyl |
| 103. | NR¹ | $CH_2$ | $CH_2$—Ph | $C_2$ | | 1,4-piperazinylene | 5-chromanyl |
| 104. | NR¹ | $CH_2$ | $CH_2$—Ph | $C_2$ | | 1,4-piperazinylene | 3-isoxazolyl |
| 105. | NR¹ | $CH_2$ | $CH_2$—Ph | $C_2$ | | 1,4-piperazinylene | 7-OMe-1-naphthyl |
| 106. | NR¹ | $CH_2$ | $CH_2$—Ph | $C_2$ | | 1,4-piperazinylene | 1-tetralinyl |
| 107. | NR¹ | $CH_2$ | $CH_2$—Ph | $C_2$ | | 1,4-piperazinylene | 2-Et-naphthyl |
| 108. | NR¹ | $CH_2$ | $CH_2$—Ph | $C_2$ | | 1,4-piperazinylene | 2-quinolinyl |
| 109. | NR¹ | $CH_2$ | Me | $C_2$ | | 1,4-piperazinylene | Ph |
| 110. | NR¹ | $CH_2$ | Me | $C_2$ | | 1,4-piperazinylene | 2-OH—Ph |
| 111. | NR¹ | $CH_2$ | Me | $C_2$ | | 1,4-piperazinylene | 2-OMe—Ph |
| 112. | NR¹ | $CH_2$ | Me | $C_2$ | | 1,4-piperazinylene | 2-Me—Ph |
| 113. | NR¹ | $CH_2$ | Me | $C_2$ | | 1,4-piperazinylene | 2-CN—Ph |
| 114. | NR¹ | $CH_2$ | Me | $C_2$ | | 1,4-piperazinylene | 2-Cl—Ph |
| 115. | NR¹ | $CH_2$ | Me | $C_2$ | Me | 1,4-piperazinylene | 3-$NR^2{}_2$—Ph |
| 116. | NR¹ | $CH_2$ | Me | $C_2$ | Me | 1,4-piperazinylene | 3-$CO_2R^2$—Ph |
| 117. | NR¹ | $CH_2$ | Me | $C_2$ | | 1,4-piperazinylene | 3-$CF_3$—Ph |
| 118. | NR¹ | $CH_2$ | Me | $C_2$ | | 1,4-piperazinylene | 3-$NO_2$—Ph |
| 119. | NR¹ | $CH_2$ | Me | $C_2$ | | 1,4-piperazinylene | 3-F—Ph |
| 120. | NR¹ | $CH_2$ | Me | $C_2$ | | 1,4-piperazinylene | 4-$iC_3$—Ph |
| 121. | NR¹ | $CH_2$ | Me | $C_2$ | | 1,4-piperazinylene | 4-I—Ph |
| 122. | NR¹ | $CH_2$ | Me | $C_2$ | | 1,4-piperazinylene | 4-Br—Ph |
| 123. | NR¹ | $CH_2$ | Me | $C_2$ | | 1,4-piperazinylene | 4-O(n-$C_4$)—Ph |
| 124. | NR¹ | $CH_2$ | Me | $C_2$ | | 1,4-piperazinylene | 4-tBu—Ph |
| 125. | NR¹ | $CH_2$ | Me | $C_2$ | H | 1,4-piperazinylene | 4-$CO_2R^2$—Ph |
| 126. | NR¹ | $CH_2$ | Me | $C_2$ | n-$C_3$ | 1,4-piperazinylene | 4-$NR^2{}_2$—Ph |
| 127. | NR¹ | $CH_2$ | Me | $C_2$ | | 1,4-piperazinylene | 3-Me, 4-Me—Ph |
| 128. | NR¹ | $CH_2$ | Me | $C_2$ | | 1,4-piperazinylene | 2-Cl, 4-$NO_2$—Ph |
| 129. | NR¹ | $CH_2$ | Me | $C_2$ | | 1,4-piperazinylene | 3-tBn, 5-$CF_3$—Ph |
| 130. | NR¹ | $CH_2$ | Me | $C_2$ | | 1,4-piperazinylene | 2-Me, 5-Ph—Ph |
| 131. | NR¹ | $CH_2$ | Me | $C_2$ | | 1,4-piperazinylene | 2-OMe, 4-Cl, 5-MePh |
| 132. | NR¹ | $CH_2$ | Me | $C_2$ | | 1,4-piperazinylene | 5-tetralinyl |
| 133. | NR¹ | $CH_2$ | Me | $C_2$ | | 1,4-piperazinylene | 4-indanyl |
| 134. | NR¹ | $CH_2$ | Me | $C_2$ | | 1,4-piperazinylene | 1-naphthyl |
| 135. | NR¹ | $CH_2$ | Me | $C_2$ | | 1,4-piperazinylene | 2-OMe-1-naphthyl |
| 136. | NR¹ | $CH_2$ | Me | $C_2$ | | 1,4-piperazinylene | 2-Me-1-naphthyl |
| 137. | NR¹ | $CH_2$ | Me | $C_2$ | | 1,4-piperazinylene | 8-OMe-1-naphthyl |
| 138. | NR¹ | $CH_2$ | Me | $C_2$ | | 1,4-piperazinylene | 3-indolyl |
| 139. | NR¹ | $CH_2$ | Me | $C_2$ | | 1,4-piperazinylene | 2-quinazolinyl |
| 140. | NR¹ | $CH_2$ | Me | $C_2$ | | 1,4-piperazinylene | 4-quinazolinyl |
| 141. | NR¹ | $CH_2$ | Me | $C_2$ | | 1,4-piperazinylene | 2-quinoxalinyl |
| 142. | NR¹ | $CH_2$ | Me | $C_2$ | | 1,4-piperazinylene | 1-phthalazinyl |
| 143. | NR¹ | $CH_2$ | Me | $C_2$ | | 1,4-piperazinylene | 4-quinolinyl |
| 144. | NR¹ | $CH_2$ | Me | $C_2$ | | 1,4-piperazinylene | 1-isoquinolinyl |
| 145. | NR¹ | $CH_2$ | Me | $C_2$ | | 1,4-piperazinylene | 4-isoquinolinyl |
| 146. | NR¹ | $CH_2$ | Me | $C_2$ | | 1,4-piperazinylene | 7-benzofuranyl |
| 147. | NR¹ | $CH_2$ | Me | $C_2$ | | 1,4-piperazinylene | 2-pyrimidinyl |
| 148. | NR¹ | $CH_2$ | Me | $C_2$ | | 1,4-piperazinylene | 2-tBu, |

-continued

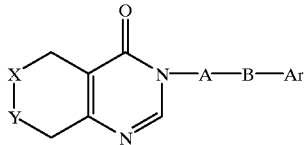

| No. | X | Y | R¹ | A | R² | B | Ar |
|---|---|---|---|---|---|---|---|
| | | | | | | | M.p. hydro-chloride |
| 149. | NR¹ | CH₂ | Me | C₂ | | 1,4-piperazinylene | 4-CF₃-6-pyrimidinyl 2-pyridinyl |
| 150. | NR¹ | CH₂ | Me | C₂ | | 1,4-piperazinylene | 2-Ph-4-quinazolinyl |
| 151. | NR¹ | CH₂ | Me | C₂ | | 1,4-piperazinylene | 5-chromanyl |
| 152. | NR¹ | CH₂ | Me | C₂ | | 1,4-piperazinylene | 3-isoxazolyl |
| 153. | NR¹ | CH₂ | Me | C₂ | | 1,4-piperazinylene | 7-OMe-1-naphthyl |
| 154. | NR¹ | CH₂ | Me | C₂ | | 1,4-piperazinylene | 1-tetralinyl |
| 155. | NR¹ | CH₂ | Me | C₂ | | 1,4-piperazinylene | 2-Et-naphthyl |
| 156. | NR¹ | CH₂ | Me | C₂ | | 1,4-piperazinylene | 2-quinolinyl |
| 157. | NR¹ | CH₂ | Boc | C₂ | | 1,4-piperazinylene | Ph |
| 158. | NR¹ | CH₂ | Boc | C₂ | | 1,4-piperazinylene | 2-OMe—Ph |
| 159. | NR¹ | CH₂ | Boc | C₂ | | 1,4-piperazinylene | 2-Me—Ph |
| 160. | NR¹ | CH₂ | Boc | C₂ | | 1,4-piperazinylene | 2-Cl—Ph |
| 161. | NR¹ | CH₂ | Boc | C₂ | | 1,4-piperazinylene | 3-CN—Ph |
| 162. | NR¹ | CH₂ | Boc | C₂ | | 1,4-piperazinylene | 4-F—Ph |
| 163. | NR¹ | CH₂ | Boc | C₂ | | 1,4-piperazinylene | 3-tBu, 5-CF₃—Ph |
| 164. | NR¹ | CH₂ | Boc | C₂ | | 1,4-piperazinylene | 5-tetralinyl |
| 165. | NR¹ | CH₂ | Boc | C₂ | | 1,4-piperazinylene | 4-indanyl |
| 166. | NR¹ | CH₂ | Boc | C₂ | | 1,4-piperazinylene | 1-naphthyl |
| 167. | NR¹ | CH₂ | Boc | C₂ | | 1,4-piperazinylene | 2-OMe-naphthyl |
| 168. | NR¹ | CH₂ | Boc | C₂ | | 1,4-piperazinylene | 2-Me-naphthyl |
| 169. | NR¹ | CH₂ | Boc | C₂ | | 1,4-piperazinylene | 8-OMe-naphthyl |
| 170. | NR¹ | CH₂ | Boc | C₂ | | 1,4-piperazinylene | 4-quinazolinyl |
| 171. | NR¹ | CH₂ | Boc | C₂ | | 1,4-piperazinylene | 2-quinazolinyl |
| 172. | NR¹ | CH₂ | Boc | C₂ | | 1,4-piperazinylene | 1-phthalazinyl |
| 173. | NR¹ | CH₂ | Boc | C₂ | | 1,4-piperazinylene | 4-quinolinyl |
| 174. | NR¹ | CH₂ | Boc | C₂ | | 1,4-piperazinylene | 4-isoquinolinyl |
| 175. | NR¹ | CH₂ | Boc | C₂ | | 1,4-piperazinylene | 2-pyrimidinyl |
| 176. | NR¹ | CH₂ | Boc | C₂ | | 1,4-piperazinylene | 2-tBu, 4-CF₃-6-pyrimidinyl |
| 177. | NR¹ | CH₂ | Boc | C₂ | | 1,4-piperazinylene | 2-pyridinyl |
| 178. | NR¹ | CH₂ | CH₃C=O | C₂ | | 1,4-piperazinylene | Ph |
| 179. | NR¹ | CH₂ | CH₃C=O | C₂ | | 1,4-piperazinylene | 2-OMe—Ph |
| 180. | NR¹ | CH₂ | CH₃C=O | C₂ | | 1,4-piperazinylene | 2-Me—Ph |
| 181. | NR¹ | CH₂ | CH₃C=O | C₂ | | 1,4-piperazinylene | 2-Cl—Ph |
| 182. | NR¹ | CH₂ | CH₃C=O | C₂ | | 1,4-piperazinylene | 3-CN—Ph |
| 183. | NR¹ | CH₂ | CH₃C=O | C₂ | | 1,4-piperazinylene | 4-F—Ph |
| 184. | NR¹ | CH₂ | CH₃C=O | C₂ | | 1,4-piperazinylene | 3-tBu, 5-CF₃—Ph |
| 185. | NR¹ | CH₂ | CH₃C=O | C₂ | | 1,4-piperazinylene | 5-tetralinyl |
| 186. | NR¹ | CH₂ | CH₃C=O | C₂ | | 1,4-piperazinylene | 4-indanyl |
| 187. | NR¹ | CH₂ | CH₃C=O | C₂ | | 1,4-piperazinylene | 1-naphthyl |
| 188. | NR¹ | CH₂ | CH₃C=O | C₂ | | 1,4-piperazinylene | 2-OMe-naphthyl |
| 189. | NR¹ | CH₂ | CH₃C=O | C₂ | | 1,4-piperazinylene | 2-Me-1-naphthyl |
| 190. | NR¹ | CH₂ | CH₃C=O | C₂ | | 1,4-piperazinylene | 8-OMe-1-naphthyl |
| 191. | NR¹ | CH₂ | CH₃C=O | C₂ | | 1,4-piperazinylene | 4-quinazolinyl |
| 192. | NR¹ | CH₂ | CH₃C=O | C₂ | | 1,4-piperazinylene | 2-quinazolinyl |
| 193. | NR¹ | CH₂ | CH₃C=O | C₂ | | 1,4-piperazinylene | 1-phthalazinyl |
| 194. | NR¹ | CH₂ | CH₃C=O | C₂ | | 1,4-piperazinylene | 4-quinolinyl |
| 195. | NR¹ | CH₂ | CH₃C=O | C₂ | | 1,4-piperazinylene | 1-isoquinoline |
| 196. | NR¹ | CH₂ | CH₃C=O | C₂ | | 1,4-piperazinylene | 2-pyrimidinyl |
| 197. | NR¹ | CH₂ | CH₃C=O | C₂ | | 1,4-piperazinylene | 2-tBu, 4-CF₃-6-pyrimidinyl |
| 198. | NR¹ | CH₂ | CH₃C=O | C₂ | | 1,4-piperazinylene | 2-pyridinyl |
| 199. | NR¹ | CH₂ | Ph—C=O | C₂ | | 1,4-piperazinylene | Ph |
| 200. | NR¹ | CH₂ | Ph—C=O | C₂ | | 1,4-piperazinylene | 2-OMe—Ph |
| 201. | NR¹ | CH₂ | Ph—C=O | C₂ | | 1,4-piperazinylene | 2-Me—Ph |
| 202. | NR¹ | CH₂ | Ph—C=O | C₂ | | 1,4-piperazinylene | 2-Cl—Ph |
| 203. | NR¹ | CH₂ | Ph—C=O | C₂ | | 1,4-piperazinylene | 3-CN—Ph |
| 204. | NR¹ | CH₂ | Ph—C=O | C₂ | | 1,4-piperazinylene | 4-F—Ph |
| 205. | NR¹ | CH₂ | Ph—C=O | C₂ | | 1,4-piperazinylene | 3-tBu,5-CF₃—Ph |
| 206. | NR¹ | CH₂ | Ph—C=O | C₂ | | 1,4-piperazinylene | 5-tetralinyl |
| 207. | NR¹ | CH₂ | Ph—C=O | C₂ | | 1,4-piperazinylene | 4-indanyl |
| 208. | NR¹ | CH₂ | Ph—C=O | C₂ | | 1,4-piperazinylene | 1-naphthyl |
| 209. | NR¹ | CH₂ | Ph—C=O | C₂ | | 1,4-piperazinylene | 2-OMe-1-naphthyl |
| 210. | NR¹ | CH₂ | Ph—C=O | C₂ | | 1,4-piperazinylene | 2-Me-1-naphthyl |
| 211. | NR¹ | CH₂ | Ph—C=O | C₂ | | 1,4-piperazinylene | 8-OMe-1-naphthyl |

-continued

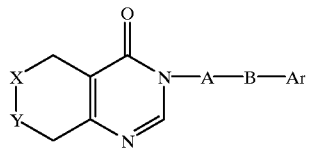

| No. | X | Y | R¹ | A | R² | B | Ar | M.p. hydro-chloride |
|---|---|---|---|---|---|---|---|---|
| 212. | NR¹ | CH$_2$ | Ph—C=O | C$_2$ | | 1,4-piperazinylene | 4-quinazolinyl | |
| 213. | NR¹ | CH$_2$ | Ph—C=O | C$_2$ | | 1,4-piperazinylene | 2-quinazolinyl | |
| 214. | NR¹ | CH$_2$ | Ph—C=O | C$_2$ | | 1,4-piperazinylene | 1-phthalazinyl | |
| 215. | NR¹ | CH$_2$ | Ph—C=O | C$_2$ | | 1,4-piperazinylene | 4-quinolinyl | |
| 216. | NR¹ | CH$_2$ | Ph—C=O | C$_2$ | | 1,4-piperazinylene | 4-isoquinolinyl | |
| 217. | NR¹ | CH$_2$ | Ph—C=O | C$_2$ | | 1,4-piperazinylene | 2-pyrimidinyl | |
| 218. | NR¹ | CH$_2$ | Ph—C=O | C$_2$ | | 1,4-piperazinylene | 2-tBu, 4-CF$_3$-pyrimidinyl | |
| 219. | NR¹ | CH$_2$ | Ph—C=O | C$_2$ | | 1,4-piperazinylene | 2-pyridinyl | |
| 220. | NR¹ | CH$_2$ | i-C$_3$ | C$_2$ | | 1,4-piperazinylene | 1-naphthyl | |
| 221. | NR¹ | CH$_2$ | C$_2$—Ph | C$_2$ | | 1,4-piperazinylene | 1-naphthyl | |
| 222. | NR¹ | CH$_2$ | C$_2$—(2-OMe)Ph | C$_2$ | | 1,4-piperazinylene | 1-naphthyl | |
| 223. | NR¹ | CH$_2$ | C$_3$—(4-Cl)Ph | C$_2$ | | 1,4-piperazinylene | 1-naphthyl | |
| 224. | NR¹ | CH$_2$ | C$_2$—(2-CF$_3$)Ph | C$_2$ | | 1,4-piperazinylene | 1-naphthyl | |
| 225. | NR¹ | CH$_2$ | H | C$_3$ | | 1,4-piperazinylene | 5-tetralinyl | |
| 226. | NR¹ | CH$_2$ | H | C$_3$ | | 1,4-piperazinylene | 1-naphthyl | |
| 227. | NR¹ | CH$_2$ | H | C$_3$ | | 1,4-piperazinylene | 2-OMe—Ph | |
| 228. | NR¹ | CH$_2$ | H | C$_3$ | | 1,4-piperazinylene | 4-isoquinolinyl | |
| 229. | NR¹ | CH$_2$ | H | C$_3$ | | 1,4-piperazinylene | 2-pyrimidinyl | |
| 230. | NR¹ | CH$_2$ | H | C$_3$ | | 1,4-piperazinylene | 2-OMe-naphthyl | |
| 231. | NR¹ | CH$_2$ | CH$_2$—Ph | C$_3$ | | 1,4-piperazinylene | 5-tetralinyl | |
| 232. | NR¹ | CH$_2$ | CH$_2$—Ph | C$_3$ | | 1,4-piperazinylene | 1-naphthyl | |
| 233. | NR¹ | CH$_2$ | CH$_2$—Ph | C$_3$ | | 1,4-piperazinylene | 2-OMe—Ph | |
| 234. | NR¹ | CH$_2$ | CH$_2$—Ph | C$_3$ | | 1,4-piperazinylene | 4-isoquinolinyl | |
| 235. | NR¹ | CH$_2$ | CH$_2$—Ph | C$_3$ | | 1,4-piperazinylene | 2-pyridinyl | |
| 236. | NR¹ | CH$_2$ | CH$_2$—Ph | C$_3$ | | 1,4-piperazinylene | 4-indane | |
| 237. | NR¹ | CH$_2$ | Me | C$_3$ | | 1,4-piperazinylene | 5-tetralinyl | |
| 238. | NR¹ | CH$_2$ | Me | C$_3$ | | 1,4-piperazinylene | 1-naphthyl | |
| 239. | NR¹ | CH$_2$ | Me | C$_3$ | | 1,4-piperazinylene | 2-OMe—Ph | |
| 240. | NR¹ | CH$_2$ | Me | C$_3$ | | 1,4-piperazinylene | 4-isoquinolinyl | |
| 241. | NR¹ | CH$_2$ | Me | C$_3$ | | 1,4-piperazinylene | 2-pyrimidinyl | |
| 242. | NR¹ | CH$_2$ | Me | C$_3$ | | 1,4-piperazinylene | 2-OMe-naphthyl | |
| 243. | NR¹ | CH$_2$ | Boc | C$_3$ | | 1,4-piperazinylene | 5-tetralinyl | |
| 244. | NR¹ | CH$_2$ | Boc | C$_3$ | | 1,4-piperazinylene | 1-naphthyl | |
| 245. | NR¹ | CH$_2$ | Boc | C$_3$ | | 1,4-piperazinylene | 2-OMe—Ph | |
| 246. | NR¹ | CH$_2$ | Boc | C$_3$ | | 1,4-piperazinylene | 4-isoquinolinyl | |
| 247. | NR¹ | CH$_2$ | Boc | C$_3$ | | 1,4-piperazinylene | 2-pyrimidinyl | |
| 248. | NR¹ | CH$_2$ | Boc | C$_3$ | | 1,4-piperazinylene | 2-OMe-naphthyl | |
| 249. | NR¹ | CH$_2$ | CH$_3$—C=O | C$_3$ | | 1,4-piperazinylene | 5-tetralinyl | |
| 250. | NR¹ | CH$_2$ | CH$_3$—C=O | C$_3$ | | 1,4-piperazinylene | 1-naphthyl | |
| 251. | NR¹ | CH$_2$ | CH$_3$—C=O | C$_3$ | | 1,4-piperazinylene | 2-OMe—Ph | |
| 252. | NR¹ | CH$_2$ | CH$_3$—C=O | C$_3$ | | 1,4-piperazinylene | 4-isoquinolinyl | |
| 253. | NR¹ | CH$_2$ | CH$_3$—C=O | C$_3$ | | 1,4-piperazinylene | 2-pyrimidinyl | |
| 254. | NR¹ | CH$_2$ | Ph—C=O | C$_3$ | | 1,4-piperazinylene | 2-OMe-naphthyl | |
| 255. | NR¹ | CH$_2$ | Ph—C=O | C$_3$ | | 1,4-piperazinylene | 5-tetralinyl | |
| 256. | NR¹ | CH$_2$ | Ph—C=O | C$_3$ | | 1,4-piperazinylene | 1-naphthyl | |
| 257. | NR¹ | CH$_2$ | Ph—C=O | C$_3$ | | 1,4-piperazinylene | 2-OMe—Ph | |
| 258. | NR¹ | CH$_2$ | Ph—C=O | C$_3$ | | 1,4-piperazinylene | 4-isoquinolinyl | |
| 259. | NR¹ | CH$_2$ | Ph—C=O | C$_3$ | | 1,4-piperazinylene | 2-pyrimidinyl | |
| 260. | NR¹ | CH$_2$ | Ph—C=O | C$_3$ | | 1,4-piperazinylene | 2-OMe-naphthyl | |
| 261. | NR¹ | CH$_2$ | H | C$_2$ | | 1,4-piperadinylene | 5-tetralinyl | |
| 262. | NR¹ | CH$_2$ | H | C$_2$ | | 1,4-piperadinylene | 1-naphthyl | |
| 263. | NR¹ | CH$_2$ | H | C$_2$ | | 1,4-piperidinylene | 2-OMe—Ph | |
| 264. | NR¹ | CH$_2$ | H | C$_2$ | | 1,4-piperidinylene | 4-isoquinolinyl | |
| 265. | NR¹ | CH$_2$ | H | C$_2$ | | 1,4-piperidinylene | 2-pyrimidinyl | |
| 266. | NR¹ | CH$_2$ | H | C$_2$ | | 1,4-piperidinylene | 2-OMe-naphthyl | |
| 267. | NR¹ | CH$_2$ | Me | C$_2$ | | 1,4-piperidinylene | 5-tetralinyl | |
| 268. | NR¹ | CH$_2$ | Me | C$_2$ | | 1,4-piperidinylene | 1-naphthyl | |
| 269. | NR¹ | CH$_2$ | Me | C$_2$ | | 1,4-piperidinylene | 2-OMe—Ph | |
| 270. | NR¹ | CH$_2$ | Me | C$_2$ | | 1,4-piperidinylene | 4-isoquinolinyl | |
| 271. | NR¹ | CH$_2$ | Me | C$_2$ | | 1,4-piperidinylene | 2-pyrimidinyl | |
| 272. | NR¹ | CH$_2$ | Me | C$_2$ | | 1,4-piperidinylene | 2-OMe-naphthyl | |
| 273. | NR¹ | CH$_2$ | CH$_2$—Ph | C$_2$ | | 1,4-piperidinylene | 5-tetralinyl | |
| 274. | NR¹ | CH$_2$ | CH$_2$—Ph | C$_2$ | | 1,4-piperidinylene | 1-naphthyl | |
| 275. | NR¹ | CH$_2$ | CH$_2$—Ph | C$_2$ | | 1,4-piperidinylene | 2-OMe—Ph | |
| 276. | NR¹ | CH$_2$ | CH$_2$—Ph | C$_2$ | | 1,4-piperidinylene | 4-isoquinolinyl | |
| 277. | NR¹ | CH$_2$ | CH$_2$—Ph | C$_2$ | | 1,4-piperidinylene | 2-pyrimidinyl | |

-continued

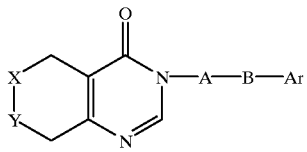

| No. | X | Y | R1 | A | R2 | B | Ar | M.p. hydro-chloride |
|---|---|---|---|---|---|---|---|---|
| 278. | NR1 | CH2 | CH2—Ph | C2 | | 1,4-piperidinylene | 2-OMe-naphthyl | |
| 279. | NR1 | CH2 | CH3C=O | C2 | | 1,4-piperidinylene | 5-tetralinyl | |
| 280. | NR1 | CH2 | CH3C=O | C2 | | 1,4-piperidinylene | 1-naphthyl | |
| 281. | NR1 | CH2 | CH3C=O | C2 | | 1,4-piperidinylene | 2-OMe-Ph | |
| 282. | NR1 | CH2 | CH3C=O | C2 | | 1,4-piperidinylene | 4-isoquinolinyl | |
| 283. | NR1 | CH2 | CH3C=O | C2 | | 1,4-piperidinylene | 2-pyrimidinyl | |
| 284. | NR1 | CH2 | CH3C=O | C2 | | 1,4-piperidinylene | 2-OMe-naphthyl | |
| 285. | NR1 | CH2 | Boc | C2 | | 1,4-piperidinylene | 5-tetralinyl | |
| 286. | NR1 | CH2 | Boc | C2 | | 1,4-piperidinylene | 1-naphthyl | |
| 287. | NR1 | CH2 | Boc | C2 | | 1,4-piperidinylene | 2-OMe-Ph | |
| 288. | NR1 | CH2 | Boc | C2 | | 1,4-piperidinylene | 4-isoquinolinyl | |
| 289. | NR1 | CH2 | Boc | C2 | | 1,4-piperidinylene | 2-pyrimidinyl | |
| 290. | NR1 | CH2 | Boc | C2 | | 1,4-piperidinylene | 2-OMe-naphthyl | |
| 291. | NR1 | CH2 | Ph—C=O | C2 | | 1,4-piperidinylene | 5-tetralinyl | |
| 292. | NR1 | CH2 | Ph—C=O | C2 | | 1,4-piperidinylene | 1-naphthyl | |
| 293. | NR1 | CH2 | Ph—C=O | C2 | | 1,4-piperidinylene | 2-OMe—Ph | |
| 294. | NR1 | CH2 | Ph—C=O | C2 | | 1,4-piperidinylene | 4-isoquinolinyl | |
| 295. | NR1 | CH2 | Ph—C=O | C2 | | 1,4-piperidinylene | 2-pyrimidinyl | |
| 296. | NR1 | CH2 | Ph—C=O | C2 | | 1,4-piperidinylene | 2-OMe-naphthyl | |
| 297. | NR1 | CH2 | H | C2 | | 1,2,3,6-tetrahydro-1,4-pyridinylene | 5-tetralinyl | |
| 298. | NR1 | CH2 | H | C2 | | 1,2,3,6-tetrahydro-1,4-pyridinylene | 1-naphthyl | |
| 299. | NR1 | CH2 | H | C2 | | 1,2,3,6-tetrahydro-1,4-pyridinylene | 2-OMe—Ph | |
| 300. | NR1 | CH2 | H | C2 | | 1,2,3,6-tetrahydro-1,4-pyridinylene | 4-isoquinolinyl | |
| 301. | NR1 | CH2 | H | C2 | | 1,2,3,6-tetrahydro-1,4-pyridinylene | 2-pyrimidinyl | |
| 302. | NR1 | CH2 | H | C2 | | 1,2,3,6-tetrahydro-1,4-pyridinylene | 2-OMe-naphthyl | |
| 303. | NR1 | CH2 | Me | C2 | | 1,2,3,6-tetrahydro-1,4-pyridinylene | 5-tetralinyl | |
| 304. | NR1 | CH2 | Me | C2 | | 1,2,3,6-tetrahydro-1,4-pyridinylene | 1-naphthyl | |
| 305. | NR1 | CH2 | Me | C2 | | 1,2,3,6-tetrahydro-1,4-pyridinylene | 2-OMe—Ph | |
| 306. | NR1 | CH2 | Me | C2 | | 1,2,3,6-tetrahydro-1,4-pyridinylene | 4-isoquinolinyl | |
| 307. | NR1 | CH2 | Me | C2 | | 1,2,3,6-tetrahydro-1,4-pyridinylene | 2-pyrimidinyl | |
| 308. | NR1 | CH2 | Me | C2 | | 1,2,3,6-tetrahydro-1,4-pyridinylene | 2-OMe-naphthyl | |
| 309. | NR1 | CH2 | CH2—Ph | C2 | | 1,2,3,6-tetrahydro-1,4-pyridinylene | tetralinyl | |
| 310. | NR1 | CH2 | CH2—Ph | C2 | | 1,2,3,6-tetrahydro-1,4-pyridinylene | 1-naphthyl | |
| 311. | NR1 | CH2 | CH2—Ph | C2 | | 1,2,3,6-tetrahydro-1,4-pyridinylene | 2-OMe—Ph | |
| 312. | NR1 | CH2 | CH2—Ph | C2 | | 1,2,3,6-tetrahydro-1,4-pyridinylene | 4-isoquinolinyl | |
| 313. | NR1 | CH2 | CH2—Ph | C2 | | 1,2,3,6-tetrahydro-1,4-pyridinylene | 2-pyrimidinyl | |
| 314. | NR1 | CH2 | CH2—Ph | C2 | | 1,2,3,6-tetrahydro-1,4-pyridinylene | 2-OMe-naphthyl | |
| 315. | NR1 | CH2 | Boc | C2 | | 1,2,3,6-tetrahydro-1,4-pyridinylene | tetralinyl | |
| 316. | NR1 | CH2 | Boc | C2 | | 1,2,3,6-tetrahydro-1,4-pyridinylene | 1-naphthyl | |
| 317. | NR1 | CH2 | Boc | C2 | | 1,2,3,6-tetrahydro-1,4-pyridinylene | 2-OMe—Ph | |
| 318. | NR1 | CH2 | Boc | C2 | | 1,2,3,6-tetrahydro-1,4-pyridinylene | 4-isoquinolinyl | |
| 319. | NR1 | CH2 | Boc | C2 | | 1,2,3,6-tetrahydro-1,4-pyridinylene | 2-pyrimidinyl | |
| 320. | NR1 | CH2 | Boc | C2 | | 1,2,3,6-tetrahydro-1,4-pyridinylene | 2-OMe-naphthyl | |
| 321. | NR1 | CH2 | CH3C=O | C2 | | 1,2,3,6-tetrahydro-1,4-pyridinylene | tetralinyl | |
| 322. | NR1 | CH2 | CH3C=O | C2 | | 1,2,3,6-tetrahydro-1,4-pyridinylene | 1-naphthyl | |
| 323. | NR1 | CH2 | CH3C=O | C2 | | 1,2,3,6-tetrahydro-1,4-pyridinylene | 2-OMe—Ph | |
| 324. | NR1 | CH2 | CH3C=O | C2 | | 1,2,3,6-tetrahydro-1,4-pyridinylene | 4-isoquinolinyl | |
| 325. | NR1 | CH2 | CH3C=O | C2 | | 1,2,3,6-tetrahydro-1,4-pyridinylene | 2-pyrimidinyl | |
| 326. | NR1 | CH2 | CH3C=O | C2 | | 1,2,3,6-tetrahydro-1,4-pyridinylene | 2-OMe-naphthyl | |
| 327. | NR1 | CH2 | Ph—C=O | C2 | | 1,2,3,6-tetrahydro-1,4-pyridinylene | tetralinyl | |
| 328. | NR1 | CH2 | Ph—C=O | C2 | | 1,2,3,6-tetrahydro-1,4-pyridinylene | 1-naphthyl | |
| 329. | NR1 | CH2 | Ph—C=O | C2 | | 1,2,3,6-tetrahydro-1,4-pyridinylene | 2-OMe—Ph | |
| 330. | NR1 | CH2 | Ph—C=O | C2 | | 1,2,3,6-tetrahydro-1,4-pyridinylene | 4-isoquinolinyl | |
| 331. | NR1 | CH2 | Ph—C=O | C2 | | 1,2,3,6-tetrahydro-1,4-pyridinylene | 2-pyrimidinyl | |
| 332. | NR1 | CH2 | Ph—C=O | C2 | | 1,2,3,6-tetrahydro-1,4-pyridinylene | 2-OMe-naphthyl | |
| 333. | NR1 | CH2 | H | C2 | | 1,4-homopiperazinylene | 1-naphthyl | |
| 334. | NR1 | CH2 | H | C2 | | 1,4-homopiperazinylene | 2-OMe—Ph | |
| 335. | NR1 | CH2 | H | C2 | | 1,4-homopiperazinylene | 2-OMe-1-naphthyl | |
| 336. | NR1 | CH2 | H | C3 | | 1,4-homopiperazinylene | 2-pyrimidinyl | |
| 337. | NR1 | CH2 | Me | C2 | | 1,4-homopiperazinylene | 1-naphthyl | |
| 338. | NR1 | CH2 | Me | C2 | | 1,4-homopiperazinylene | 2-OMe—Ph | |
| 339. | NR1 | CH2 | CH2—Ph | C2 | | 1,4-homopiperazinylene | 1-naphthyl | |
| 340. | NR1 | CH2 | CH2—Ph | C2 | | 1,4-homopiperazinylene | 2-OMe—Ph | |
| 341. | NR1 | CH2 | Boc | C2 | | 1,4-homopiperazinylene | 1-naphthyl | |
| 342. | NR1 | CH2 | Boc | C2 | | 1,4-homopiperazinylene | 2-OMe—Ph | |
| 343. | NR1 | CH2 | Boc | C3 | | 1,4-homopiperazinylene | 2-OMe-1-naphthyl | |

-continued

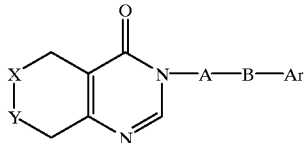

| No. | X | Y | R¹ | A | R² | B | Ar | M.p. hydrochloride |
|---|---|---|---|---|---|---|---|---|
| 344. | NR¹ | CH₂ | CH₃—C=O | C₂ | | 1,4-homopiperazinylene | 1-naphthyl | |
| 345. | NR¹ | CH₂ | CH₃—C=O | C₂ | | 1,4-homopiperazinylene | 2-OMe—Ph | |
| 346. | NR¹ | CH₂ | Ph—C=O | C₂ | | 1,4-homopiperazinylene | 1-naphthyl | |
| 347. | NR¹ | CH₂ | Ph—C=O | C₂ | | 1,4-homopiperazinylene | 1-OMe—Ph | |
| 348. | NR¹ | CH₂ | Ph—C=O | C₂ | | 1,4-homopiperazinylene | 2-pyrimidinyl | |
| 349. | NR¹ | CH₂ | H | C₂ | | 1,4-homopiperadinylene | 1-naphthyl | |
| 350. | NR¹ | CH₂ | H | C₂ | | 1,4-homopiperadinylene | 2-OMe—Ph | |
| 351. | NR¹ | CH₂ | H | C₂ | | 1,4-homopiperadinylene | 2-OMe-1-naphthyl | |
| 352. | NR¹ | CH₂ | H | C₃ | | 1,4-homopiperadinylene | 2-pyrimidinyl | |
| 353. | NR¹ | CH₂ | Me | C₂ | | 1,4-homopiperidinylene | 1-naphthyl | |
| 354. | NR¹ | CH₂ | Me | C₂ | | 1,4-homopiperidinylene | 2-OMe—Ph | |
| 355. | NR¹ | CH₂ | CH₂—Ph | C₂ | | 1,4-homopiperidinylene | 1-naphthyl | |
| 356. | NR¹ | CH₂ | CH₂—Ph | C₂ | | 1,4-homopiperidinylene | 2-OMe—Ph | |
| 357. | NR¹ | CH₂ | Boc | C₂ | | 1,4-homopiperidinylene | 1-naphthyl | |
| 358. | NR¹ | CH₂ | Boc | C₂ | | 1,4-homopiperidinylene | 2-OMe—Ph | |
| 359. | NR¹ | CH₂ | Boc | C₃ | | 1,4-homopiperidinylene | 2-OMe-1-naphthyl | |
| 360. | NR¹ | CH₂ | CH₃—C=O | C₂ | | 1,4-homopiperidinylene | 1-naphthyl | |
| 361. | NR¹ | CH₂ | CH₃—C=O | C₂ | | 1,4-homopiperidinylene | 2-OMe—Ph | |
| 362. | NR¹ | CH₂ | Ph—C=O | C₂ | | 1,4-homopiperidinylene | 1-naphthyl | |
| 363. | NR¹ | CH₂ | Ph—C=O | C₂ | | 1,4-homopiperidinylene | 2-OMe—Ph | |
| 364. | NR¹ | CH₂ | Ph—C=O | C₂ | | 1,4-homopiperidinylene | 2-pyrimidinyl | |
| 365. | NR¹ | CH₂ | H | C₂ | | tetrahydro-2H-azepinylene | 1-naphthyl | |
| 366. | NR¹ | CH₂ | H | C₂ | | tetrahydro-2H-azepinylene | 2-OMe—Ph | |
| 367. | NR¹ | CH₂ | H | C₂ | | tetrahydro-2H-azepinylene | 2-OMe-1-naphthyl | |
| 368. | NR¹ | CH₂ | H | C₃ | | tetrahydro-2H-azepinylene | 2-pyrimidinyl | |
| 369. | NR¹ | CH₂ | Me | C₂ | | tetrahydro-2H-azepinylene | 1-naphthyl | |
| 370. | NR¹ | CH₂ | H | C₂ | | tetrahydro-2H-azepinylene | 2-OMe—Ph | |
| 371. | NR¹ | CH₂ | CH₂—Ph | C₂ | | tetrahydro-2H-azepinylene | 1-naphthyl | |
| 372. | NR¹ | CH₂ | CH₂—Ph | C₂ | | tetrahydro-2H-azepinylene | 2-OMe—Ph | |
| 373. | NR¹ | CH₂ | Boc | C₂ | | tetrahydro-2H-azepinylene | 1-naphthyl | |
| 374. | NR¹ | CH₂ | Boc | C₂ | | tetrahydro-2H-azepinylene | 2-OMe—Ph | |
| 375. | NR¹ | CH₂ | Boc | C₃ | | tetrahydro-2H-azepinylene | 2-OMe-1-naphthyl | |
| 376. | NR¹ | CH₂ | CH₃—C=O | C₂ | | tetrahydro-2H-azepinylene | 1-naphthyl | |
| 377. | NR¹ | CH₂ | CH₃—C=O | C₂ | | tetrahydro-2H-azepinylene | 2-OMe—Ph | |
| 378. | NR¹ | CH₂ | Ph—C=O | C₂ | | tetrahydro-2H-azepinylene | 1-naphthyl | |
| 379. | NR¹ | CH₂ | Ph—C=O | C₂ | | tetrahydro-2H-azepinylene | 2-OMe—Ph | |
| 380. | NR¹ | CH₂ | Ph—C=O | C₂ | | tetrahydro-2H-azepinylene | 2-pyrimidinyl | |
| 381. | NR¹ | CH₂ | H | CH₂—C(CH₂)—CH₂ | | 1,4-piperazinylene | 2-OMe—Ph | |
| 382. | NR¹ | CH₂ | H | CH₂—C(CH₂)—CH₂ | | 1,4-piperazinylene | 1-naphthyl | |
| 383. | NR¹ | CH₂ | H | CH₂—C(CH₂)—CH₂ | | 1,4-piperidinylene | 1-naphthyl | |
| 384. | NR¹ | CH₂ | Me | CH₂—C(CH₂)—CH₂ | | 1,4-piperazinylene | 2-OMe—Ph | |
| 385. | NR¹ | CH₂ | Me | CH₂—C(CH₂)—CH₂ | | 1,4-piperazinylene | 1-naphthyl | |
| 386. | NR¹ | CH₂ | Me | CH₂—C(CH₂)—CH₂ | | 1,4-homopiperazinylene | 1-naphthyl | |
| 387. | NR¹ | CH₂ | CH₂—Ph | CH₂—C(CH₂)—CH₂ | | 1,4-piperazinylene | 2-OMe—Ph | |
| 388. | NR¹ | CH₂ | CH₂—Ph | CH₂—C(CH₂)—CH₂ | | 1,4-piperazinylene | 1-naphthyl | |
| 389. | NR¹ | CH₂ | CH₂—Ph | CH₂—C(CH₂)—CH₂ | | 1,2,3,6-tetrahydro-1,4-pyridinylene | 1-naphthyl | |
| 390. | NR¹ | CH₂ | Boc | CH₂—C(CH₂)—CH₂ | | 1,4-piperazinylene | 2-OMe—Ph | |
| 391. | NR¹ | CH₂ | Boc | CH₂—C(CH₂)—CH₂ | | 1,4-piperazinylene | 1-naphthyl | |
| 392. | NR¹ | CH₂ | Boc | CH₂—C(CH₂)—CH₂ | | 1,4-piperazinylene | 2-pyrimidinyl | |
| 393. | NR¹ | CH₂ | CH₂—C=O | CH₂—C(CH₂)—CH₂ | | 1,4-piperazinylene | 2-OMe—Ph | |
| 394. | NR¹ | CH₂ | CH₂—C=O | CH₂—C(CH₂)—CH₂ | | 1,4-piperazinylene | 1-naphthyl | |
| 395. | NR¹ | CH₂ | Ph—C=O | CH₂—C(CH₂)—CH₂ | | 1,4-piperazinylene | 2-OMe—Ph | |
| 396. | NR¹ | CH₂ | Ph—C=O | CH₂—C(CH₂)—CH₂ | | 1,4-piperazinylene | 1-naphthyl | |
| 397. | NR¹ | CH₂ | H | CH₂—C(OH)—CH₂ | | 1,4-piperazinylene | 2-OMe—Ph | |
| 398. | NR¹ | CH₂ | H | CH₂—C(OH)—CH₂ | | 1,4-piperazinylene | 1-naphthyl | |
| 399. | NR¹ | CH₂ | H | CH₂—C(OH)—CH₂ | | 1,4-piperidinylene | 1-naphthyl | |
| 400. | NR¹ | CH₂ | Me | CH₂—C(OH)—CH₂ | | 1,4-piperazinylene | 2-OMe—Ph | |
| 401. | NR¹ | CH₂ | H | CH₂—C(OH)—CH₂ | | 1,4-piperazinylene | 1-naphthyl | |
| 402. | NR¹ | CH₂ | H | CH₂—C(OH)—CH₂ | | 1,4-homopiperazinylene | 1-naphthyl | |
| 403. | NR¹ | CH₂ | CH₂—Ph | CH₂—C(OH)—CH₂ | | 1,4-piperazinylene | 2-OMe—Ph | |
| 404. | NR¹ | CH₂ | CH₂—Ph | CH₂—C(OH)—CH₂ | | 1,4-piperazinylene | 1-naphthyl | |
| 405. | NR¹ | CH₂ | CH₂—Ph | CH₂—C(OH)—CH₂ | | 1,2,3,6-tetrahydro-1,4-pyridinylene | 1-naphthyl | |
| 406. | NR¹ | CH₂ | CH₂—Ph | CH₂—C(OH)—CH₂ | | 1,4-piperazinylene | 2-OMe—Ph | |
| 407. | NR¹ | CH₂ | Boc | CH₂—C(OH)—CH₂ | | 1,4-piperazinylene | 1-naphthyl | |
| 408. | NR¹ | CH₂ | Boc | CH₂—C(OH)—CH₂ | | 1,4-piperazinylene | 2-pyrimidinyl | |
| 409. | NR¹ | CH₂ | CH₃—C=O | CH₂—C(OH)—CH₂ | | 1,4-piperazinylene | 2-OMe—Ph | |

-continued

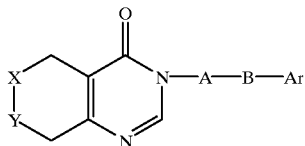

| No. | X | Y | R¹ | A | R² | B | Ar | M.p. hydro-chloride |
|---|---|---|---|---|---|---|---|---|
| 410. | NR¹ | CH₂ | CH₃—C=O | CH₂—C(OH)—CH₂ | | 1,4-piperazinylene | 1-naphthyl | |
| 411. | NR¹ | CH₂ | Ph—C=O | CH₂—C(OH)—CH₂ | | 1,4-piperazinylene | 2-OMe—Ph | |
| 412. | NR¹ | CH₂ | Ph—C=O | CH₂—C(OH)—CH₂ | | 1,4-piperazinylene | 1-naphthyl | |
| 413. | NR¹ | CH₂ | H | C₂—N(Me)—C₂ | | 1,4-piperazinylene | 2-OMe—Ph | |
| 414. | NR¹ | CH₂ | H | C₂—N(Me)—C₂ | | 1,4-piperazinylene | 1-naphthyl | |
| 415. | NR¹ | CH₂ | H | C₂—N(Me)—C₂ | | 1,4-piperidinylene | 1-naphthyl | |
| 416. | NR¹ | CH₂ | Me | C₂—N(Me)—C₂ | | 1,4-piperazinylene | 2-OMe—Ph | |
| 417. | NR¹ | CH₂ | Me | C₂—N(Me)—C₂ | | 1,4-piperazinylene | 1-naphthyl | |
| 418. | NR¹ | CH₂ | Me | C₂—N(Me)—C₂ | | 1,4-homopiperazinylene | 1-naphthyl | |
| 419. | NR¹ | CH₂ | CH₂—Ph | C₂—N(Me)—C₂ | | 1,4-piperazinylene | 2-OMe—Ph | |
| 420. | NR¹ | CH₂ | CH₂—Ph | C₂—N(Me)—C₂ | | 1,4-piperazinylene | 1-naphthyl | |
| 421. | NR¹ | CH₂ | CH₂—Ph | C₂—N(Me)—C₂ | | 1,2,3,6-tetrahydro-1,4-pyridinylene | 1-naphthyl | |
| 422. | NR¹ | CH₂ | Boc | C₂—N(Me)—C₂ | | 1,4-piperazinylene | 2-OMe—Ph | |
| 423. | NR¹ | CH₂ | Boc | C₂—N(Me)—C₂ | | 1,4-piperazinylene | 1-naphthyl | |
| 424. | NR¹ | CH₂ | Boc | C₂—N(Me)—C₂ | | 1,4-piperazinylene | 2-pyrimidinyl | |
| 425. | NR¹ | CH₂ | CH₃—C=O | C₂—N(Me)—C₂ | | 1,4-piperazinylene | 2-OMe—Ph | |
| 426. | NR¹ | CH₂ | CH₃—C=O | C₂—N(Me)—C₂ | | 1,4-piperazinylene | 1-naphthyl | |
| 427. | NR¹ | CH₂ | Ph—C=O | C₂—N(Me)—C₂ | | 1,4-piperazinylene | 2-OMe—Ph | |
| 428. | NR¹ | CH₂ | Ph—C=O | C₂—N(Me)—C₂ | | 1,4-piperazinylene | 1-naphthyl | |
| 429. | NR¹ | CH₂ | H | CH₂—CH(CH₃)—CH₂ | | 1,4-piperazinylene | 2-OMe—Ph | |
| 430. | NR¹ | CH₂ | H | CH₂—CH(CH₃)—CH₂ | | 1,4-piperazinylene | 1-naphthyl | |
| 431. | NR¹ | CH₂ | H | CH₂—CH(CH₃)—CH₂ | | 1,4-piperadinylene | 1-naphthyl | |
| 432. | NR¹ | CH₂ | Me | CH₂—CH(CH₃)—CH₂ | | 1,4-piperazinylene | 2-OMe—Ph | |
| 433. | NR¹ | CH₂ | Me | CH₂—CH(CH₃)—CH₂ | | 1,4-piperazinylene | 1-naphthyl | |
| 434. | NR¹ | CH₂ | Me | CH₂—CH(CH₃)—CH₂ | | 1,4-homopiperazinylene | 1-naphthyl | |
| 435. | NR¹ | CH₂ | CH₂—Ph | CH₂—CH(CH₃)—CH₂ | | 1,4-piperazinylene | 2-OMe—Ph | |
| 436. | NR¹ | CH₂ | CH₂—Ph | CH₂—CH(CH₃)—CH₂ | | 1,4-piperazinylene | 1-naphthyl | |
| 437. | NR¹ | CH₂ | CH₂—Ph | CH₂—CH(CH₃)—CH₂ | | 1,2,3,6-tetrahydro-1,4-pyridinylene | 1-naphthyl | |
| 438. | NR¹ | CH₂ | Boc | CH₂—CH(CH₃)—CH₂ | | 1,4-piperazinylene | 2-OMe—Ph | |
| 439. | NR¹ | CH₂ | Boc | CH₂—CH(CH₃)—CH₂ | | 1,4-piperazinylene | 1-naphthyl | |
| 440. | NR¹ | CH₂ | Boc | CH₂—CH(CH₃)—CH₂ | | 1,4-piperazinylene | 2-pyrimidinylene | |
| 441. | NR¹ | CH₂ | CH₃—C=O | CH₂—CH(CH₃)—CH₂ | | 1,4-piperazinylene | 2-OMe—Ph | |
| 442. | NR¹ | CH₂ | CH₃—C=O | CH₂—CH(CH₃)—CH₂ | | 1,4-piperazinylene | 1-naphthyl | |
| 443. | NR¹ | CH₂ | Ph—C=O | CH₂—CH(CH₃)—CH₂ | | 1,4-piperazinylene | 2-OMe—Ph | |
| 444. | NR¹ | CH₂ | Ph—C=O | CH₂—CH(CH₃)—CH₂ | | 1,4-piperazinylene | 1-naphthyl | |
| 445. | CH₂ | NR¹ | CH₂—Ph | C₂ | | 1,4-piperazinylene | Ph | |
| 446. | CH₂ | NR¹ | CH₂—Ph | C₂ | | 1,4-piperazinylene | 2-OMe—Ph | |
| 447. | CH₂ | NR¹ | CH₂—Ph | C₂ | | 1,4-piperazinylene | 2-Me—Ph | |
| 448. | CH₂ | NR¹ | CH₂—Ph | C₂ | | 1,4-piperazinylene | 2-CN—Ph | |
| 449. | CH₂ | NR¹ | CH₂—Ph | C₂ | | 1,4-piperazinylene | 2-Cl—Ph | |
| 450. | CH₂ | NR¹ | CH₂—Ph | C₂ | | 1,4-piperazinylene | 3-CF₃—Ph | |
| 451. | CH₂ | NR¹ | CH₂—Ph | C₂ | | 1,4-piperazinylene | 4-iC₃—Ph | |
| 452. | CH₂ | NR¹ | CH₂—Ph | C₂ | | 1,4-piperazinylene | 3-Me, 4-Me—Ph | |
| 453. | CH₂ | NR¹ | CH₂—Ph | C₂ | | 1,4-piperazinylene | 5-tetralinyl | |
| 454. | CH₂ | NR¹ | CH₂—Ph | C₂ | | 1,4-piperazinylene | 4-indanyl | |
| 455. | CH₂ | NR¹ | CH₂—Ph | C₂ | | 1,4-piperazinylene | 1-naphthyl | |
| 456. | CH₂ | NR¹ | CH₂—Ph | C₂ | | 1,4-piperazinylene | 2-OMe-1-naphthyl | |
| 457. | CH₂ | NR¹ | CH₂—Ph | C₂ | | 1,4-piperazinylene | 2-Me-1-naphthyl | |
| 458. | CH₂ | NR¹ | CH₂—Ph | C₂ | | 1,4-piperazinylene | 8-OMe-1-naphthyl | |
| 459. | CH₂ | NR¹ | CH₂—Ph | C₂ | | 1,4-piperazinylene | 2-quinazolinyl | |
| 460. | CH₂ | NR¹ | CH₂—Ph | C₂ | | 1,4-piperazinylene | 1-phthalazinyl | |
| 461. | CH₂ | NR¹ | CH₂—Ph | C₂ | | 1,4-piperazinylene | 4-quinolinyl | |
| 462. | CH₂ | NR¹ | CH₂—Ph | C₂ | | 1,4-piperazinylene | 4-isoquinolinyl | |
| 463. | CH₂ | NR¹ | CH₂—Ph | C₂ | | 1,4-piperazinylene | 2-pyrimidinyl | |
| 464. | CH₂ | NR¹ | CH₂—Ph | C₂ | | 1,4-piperazinylene | 2-pyridinyl | |
| 465. | CH₂ | NR¹ | H | C₂ | | 1,4-piperazinylene | 2-OMe—Ph | |
| 466. | CH₂ | NR¹ | H | C₂ | | 1,4-piperazinylene | 2-F—Ph | |
| 467. | CH₂ | NR¹ | H | C₂ | | 1,4-piperazinylene | 3-tBu—Ph | |
| 468. | CH₂ | NR¹ | H | C₂ | | 1,4-piperazinylene | 5-tetralinyl | |
| 469. | CH₂ | NR¹ | H | C₂ | | 1,4-piperazinylene | 1-naphthyl | |
| 470. | CH₂ | NR¹ | H | C₂ | | 1,4-piperazinylene | 2-OMe-1-naphthyl | |
| 471. | CH₂ | NR¹ | H | C₂ | | 1,4-piperazinylene | 2-Me-1-naphthyl | |
| 472. | CH₂ | NR¹ | H | C₂ | | 1,4-piperazinylene | 1-isoquinolinyl | |
| 473. | CH₂ | NR¹ | H | C₂ | | 1,4-piperazinylene | 2-Ph-4-quinazolinyl | |
| 474. | CH₂ | NR¹ | Me | C₂ | | 1,4-piperazinylene | 2-OMe—Ph | |
| 475. | CH₂ | NR¹ | Me | C₂ | | 1,4-piperazinylene | 1-naphthyl | |

-continued

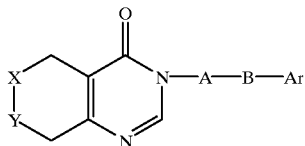

| No. | X | Y | R¹ | A | R² | B | Ar |
|---|---|---|---|---|---|---|---|
| 476. | $CH_2$ | $NR^1$ | Me | $C_2$ | | 1,4-piperazinylene | 2-Me-1-naphthyl |
| 477. | $CH_2$ | $NR^1$ | Me | $C_2$ | | 1,4-piperazinylene | 2-pyrimidinyl |
| 478. | $CH_2$ | $NR^1$ | $CH_3C=O$ | $C_2$ | | 1,4-piperazinylene | 2-OMe—Ph |
| 479. | $CH_2$ | $NR^1$ | $CH_3C=O$ | $C_2$ | | 1,4-piperazinylene | 1-naphthyl |
| 480. | $CH_2$ | $NR^1$ | PhC=O | $C_2$ | | 1,4-piperazinylene | 2-OMe—Ph |
| 481. | $CH_2$ | $NR^1$ | PhC=O | $C_2$ | | 1,4-piperazinylene | 1-naphthyl |
| 482. | $CH_2$ | $NR^1$ | Boc | $C_2$ | | 1,4-piperazinylene | 2-OMe—Ph |
| 483. | $CH_2$ | $NR^1$ | Boc | $C_2$ | | 1,4-piperazinylene | 1-naphthyl |
| 484. | $CH_2$ | $NR^1$ | $CH_2$—Ph | $C_3$ | | 1,4-piperazinylene | 2-OMe—Ph |
| 485. | $CH_2$ | $NR^1$ | $CH_2$—Ph | $C_3$ | | 1,4-piperazinylene | 1-naphthyl |
| 486. | $CH_2$ | $NR^1$ | H | $C_3$ | | 1,4-piperazinylene | 2-OMe—Ph |
| 487. | $CH_2$ | $NR^1$ | H | $C_3$ | | 1,4-piperazinylene | 1-naphthyl |
| 488. | $CH_2$ | $NR^1$ | Me | $C_3$ | | 1,4-piperazinylene | 2-OMe—Ph |
| 489. | $CH_2$ | $NR^1$ | Me | $C_3$ | | 1,4-piperazinylene | 1-naphthyl |
| 490. | $CH_2$ | $NR^1$ | Boc | $C_3$ | | 1,4-piperazinylene | 2-OMe—Ph |
| 491. | $CH_2$ | $NR^1$ | Boc | $C_3$ | | 1,4-piperazinylene | 1-naphthyl |
| 492. | $CH_2$ | $NR^1$ | $CH_3C=O$ | $C_3$ | | 1,4-piperazinylene | 2-OMe—Ph |
| 493. | $CH_2$ | $NR^1$ | $CH_3C=O$ | $C_3$ | | 1,4-piperazinylene | 1-naphthyl |
| 494. | $CH_2$ | $NR^1$ | PhC=O | $C_3$ | | 1,4-piperazinylene | 2-OMe—Ph |
| 495. | $CH_2$ | $NR^1$ | PhC=O | $C_3$ | | 1,4-piperazinylene | 1-naphthyl |
| 496. | $CH_2$ | $NR^1$ | $CH_2$—Ph | $C_2$—N(Me)—$C_2$ | | 1,4-piperazinylene | 1-naphthyl |
| 497. | $CH_2$ | $NR^1$ | H | $C_2$—N(Me)—$C_2$ | | 1,4-piperazinylene | 1-naphthyl |
| 498. | $CH_2$ | $NR^1$ | Me | $C_2$—N(Me)—$C_2$ | | 1,4-piperazinylene | 1-naphthyl |
| 499. | $CH_2$ | $NR^1$ | Boc | $C_2$—N(Me)—$C_2$ | | 1,4-piperazinylene | 1-naphthyl |
| 500. | $CH_2$ | $NR^1$ | $CH_2$—Ph | $CH_2$—C($CH_2$)—$CH_2$ | | 1,4-piperazinylene | 1-naphthyl |
| 501. | $CH_2$ | $NR^1$ | H | $CH_2$—C($CH_2$)—$CH_2$ | | 1,4-piperazinylene | 1-naphthyl |
| 502. | $CH_2$ | $NR^1$ | Me | $CH_2$—C($CH_2$)—$CH_2$ | | 1,4-piperazinylene | 1-naphthyl |
| 503. | $CH_2$ | $NR^1$ | Boc | $CH_2$—C($CH_2$)—$CH_2$ | | 1,4-piperazinylene | 1-naphthyl |
| 504. | $CH_2$ | $NR^1$ | $CH_2$—Ph | $CH_2$—CH(OH)—$CH_2$ | | 1,4-piperazinylene | 1-naphthyl |
| 505. | $CH_2$ | $NR^1$ | H | $CH_2$—CH(OH)—$CH_2$ | | 1,4-piperazinylene | 1-naphthyl |
| 506. | $CH_2$ | $NR^1$ | Me | $CH_2$—CH(OH)—$CH_2$ | | 1,4-piperazinylene | 1-naphthyl |
| 507. | $CH_2$ | $NR^1$ | Boc | $CH_2$—CH(OH)—$CH_2$ | | 1,4-piperazinylene | 1-naphthyl |
| 508. | $CH_2$ | $NR^1$ | $CH_2$—Ph | $CH_2$—CH($CH_3$)$CH_2$ | | 1,4-piperazinylene | 1-naphthyl |
| 509. | $CH_2$ | $NR^1$ | H | $CH_2$—CH($CH_3$)$CH_2$ | | 1,4-piperazinylene | 1-naphthyl |
| 510. | $CH_2$ | $NR^1$ | Me | $CH_2$—CH($CH_3$)$CH_2$ | | 1,4-piperazinylene | 1-naphthyl |
| 511. | $CH_2$ | $NR^1$ | Boc | $CH_2$—CH($CH_3$)$CH_2$ | | 1,4-piperazinylene | 1-naphthyl |
| 512. | $CH_2$ | $NR^1$ | $CH_2$—Ph | $C_2$ | | 1,4-piperidinylene | 5-tetralinyl |
| 513. | $CH_2$ | $NR^1$ | $CH_2$—Ph | $C_2$ | | 1,4-piperidinylene | 1-naphthyl |
| 514. | $CH_2$ | $NR^1$ | $CH_2$—Ph | $C_2$ | | 1,4-piperidinylene | 2-OMe—Ph |
| 515. | $CH_2$ | $NR^1$ | $CH_2$—Ph | $C_2$ | | 1,4-piperidinylene | 4-isoquinolinyl |
| 516. | $CH_2$ | $NR^1$ | $CH_2$—Ph | $C_2$ | | 1,4-piperidinylene | 2-pyrimidinyl |
| 517. | $CH_2$ | $NR^1$ | $CH_2$—Ph | $C_2$ | | 1,4-piperidinylene | 2-OMe-naphthyl |
| 518. | $CH_2$ | $NR^1$ | H | $C_2$ | | 1,4-piperidinylene | 5-tetralinyl |
| 519. | $CH_2$ | $NR^1$ | H | $C_2$ | | 1,4-piperidinylene | 1-naphthyl |
| 520. | $CH_2$ | $NR^1$ | H | $C_2$ | | 1,4-piperidinylene | 2-OMe—Ph |
| 521. | $CH_2$ | $NR^1$ | H | $C_2$ | | 1,4-piperidinylene | 4-isoquinolinyl |
| 522. | $CH_2$ | $NR^1$ | H | $C_2$ | | 1,4-pipendinylene | 2-pyrimidinyl |
| 523. | $CH_2$ | $NR^1$ | H | $C_2$ | | 1,4-piperidinylene | 2-OMe-naphthyl |
| 524. | $CH_2$ | $NR^1$ | Me | $C_2$ | | 1,4-piperidinylene | 2-OMe—Ph |
| 525. | $CH_2$ | $NR^1$ | Me | $C_2$ | | 1,4-piperidinylene | 1-naphthyl |
| 526. | $CH_2$ | $NR^1$ | Me | $C_3$ | | 1,4-piperidinylene | 2-pyrimidinyl |
| 527. | $CH_2$ | $NR^1$ | $CH_3$—C=O | $C_2$ | | 1,4-piperidinylene | 2-OMe—Ph |
| 528. | $CH_2$ | $NR^1$ | $CH_3$—C=O | $C_2$ | | 1,4-piperidinylene | 1-naphthyl |
| 529. | $CH_2$ | $NR^1$ | Ph—C=O | $C_2$ | | 1,4-piperidinylene | 2-OMe—Ph |
| 530. | $CH_2$ | $NR^1$ | Ph—C=O | $C_2$ | | 1,4-piperidinylene | 1-naphthyl |
| 531. | $CH_2$ | $NR^1$ | $CH_2$—Ph | $C_2$ | | 1,2,3,6-tetrahydro-1,4-pyridinylene | 5-tetralinyl |
| 532. | $CH_2$ | $NR^1$ | $CH_2$—Ph | $C_2$ | | 1,2,3,6-tetrahydro-1,4-pyridinylene | 1-naphthyl |
| 533. | $CH_2$ | $NR^1$ | $CH_2$—Ph | $C_2$ | | 1,2,3,6-tetrahydro-1,4-pyridinylene | 2-OMe—Ph |
| 534. | $CH_2$ | $NR^1$ | $CH_2$—Ph | $C_2$ | | 1,2,3,6-tetrahydro-1,4-pyridinylene | 4-isoquinolinyl |
| 535. | $CH_2$ | $NR^1$ | $CH_2$—Ph | $C_2$ | | 1,2,3,6-tetrahydro-1,4-pyridinylene | 2-pyrimidinyl |
| 536. | $CH_2$ | $NR^1$ | $CH_2$—Ph | $C_2$ | | 1,2,3,6-tetrahydro-1,4-pyridinylene | 2-OMe-naphthyl |
| 537. | $CH_2$ | $NR^1$ | H | $C_2$ | | 1,2,3,6-tetrahydro-1,4-pyridinylene | 1-naphthyl |
| 538. | $CH_2$ | $NR^1$ | Me | $C_2$ | | 1,2,3,6-tetrahydro-1,4-pyridinylene | 1-naphthyl |
| 539. | $CH_2$ | $NR^1$ | Boc | $C_2$ | | 1,2,3,6-tetrahydro-1,4-pyridinylene | 1-naphthyl |
| 540. | $CH_2$ | $NR^1$ | $CH_3$—C=O | $C_2$ | | 1,2,3,6-tetrahydro-1,4-pyridinylene | 1-naphthyl |
| 541. | $CH_2$ | $NR^1$ | Ph—C=O | $C_2$ | | 1,2,3,6-tetrahydro-1,4-pyridinylene | 1-naphthyl |

-continued

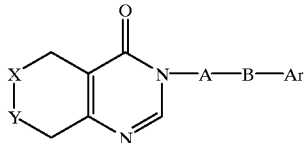

| No. | X | Y | R¹ | A | R² | B | Ar | M.p. hydrochloride |
|---|---|---|---|---|---|---|---|---|
| 542. | CH₂ | NR¹ | CH₂—Ph | C₂ | | 1,4-homopiperazinylene | 1-naphthyl | |
| 543. | CH₂ | NR¹ | H | C₂ | | 1,4-homopiperazinylene | 1-naphthyl | |
| 544. | CH₂ | NR¹ | Me | C₂ | | 1,4-homopiperazinylene | 1-naphthyl | |
| 545. | CH₂ | NR¹ | Boc | C₂ | | 1,4-homopiperazinylene | 1-naphthyl | |
| 546. | CH₂ | NR¹ | CH₂—Ph | C₂ | | azepan | 1-naphthyl | |
| 547. | CH₂ | NR¹ | H | C₂ | | azepan | 1-naphthyl | |
| 548. | CH₂ | NR¹ | Me | C₂ | | azepan | 1-naphthyl | |
| 549. | CH₂ | NR¹ | Boc | C₂ | | azepan | 1-naphthyl | |
| 550. | CH₂ | NR¹ | CH₂—Ph | C₂ | | tetrahydro-2H-azepinylene | 1-naphthyl | |
| 551. | CH₂ | NR¹ | H | C₂ | | tetrahydro-2H-azepinylene | 1-naphthyl | |
| 552. | CH₂ | NR¹ | Me | C₂ | | tetrahydro-2H-azepinylene | 1-naphthyl | |
| 553. | CH₂ | NR¹ | Boc | C₈ | | tetrahydro-2H-azepinylene | 1-naphthyl | |
| 554. | CH₂ | NR¹ | CH₂—Ph | C₂ | | tetrahydro-2H-azepinylene | 1-naphthyl | |
| 555. | NR¹ | CH₂ | CH₂—Ph | C₂ | | tetrahydro-2H-azepinylene | 1-naphthyl | |
| 556. | NR¹ | CH₂ | Me | C₂ | | 1,4-piperazinylene | 1-naphthyl | 235° C. |
| 557. | NR¹ | CH₂ | CH₃—C=O | C₂ | | 1,4-piperazinylene | 1-naphthyl | 236° C. |
| 558. | NR¹ | CH₂ | Ph—C=O | C₂ | | 1,4-piperazinylene | 1-naphthyl | 245° C. |
| 559. | NR¹ | CH₂ | Boc | C₂ | | 1,4-piperazinylene | 4-quinazolinyl | 270° C. |
| 560. | NR¹ | CH₂ | H | C₂ | | 1,4-piperazinylene | 4-quinazolinyl | 260° C. |
| 561. | NR¹ | CH₂ | Boc | C₂ | | 1,4-piperazinylene | 4-isoquinolinyl | 286° C. |
| 562. | NR¹ | CH₂ | H | C₂ | | 1,4-piperazinylene | 4-isoquinolinyl | 290° C. |
| 563. | NR¹ | CH₂ | Ph—CH₂ | C₄ | | 1,4-piperazinylene | 2-pyrimidinyl | 265° C. |
| 564. | NR¹ | CH₂ | Ph—CH₂ | C₃ | | 1,4-piperazinylene | 4-indanyl | 281° C. |
| 565. | NR¹ | CH₂ | Ph—CH₂ | C₂ | | 1,4-piperazinylene | 2-Cl—Ph | 225° C. |
| 566. | NR¹ | CH₂ | Ph—CH₂ | C₂ | | 1,4-piperazinylene | 2-pyrimidinyl | 250° C. |

We claim:

1. A compound of the formula I

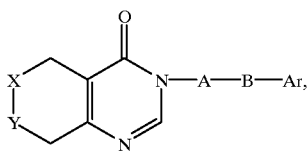

(I)

where one of the two radicals X and Y is $CH_2$ and the other is $NR^1$, $R^1$ is hydrogen, $(C_{1-8})$ alkyl branched or unbranched, CO—$(C_{1-4})$-alkyl, $CO_2tBu$, CO-aryl and a phenylalkyl-$C_1$–$C_4$ radical which in turn may be substituted on the aromatic system by F, Cl, Br, I, $C_1$–$C_4$ alkyl, $C_1$–$C_4$ alkoxy, trifluoromethyl, hydroxyl, amino, cyano or nitro, A is branched or unbranched $(C_{1-10})$-alkylene or straight-chain or branched $(C_{2-10})$-alkylene which comprises at least one group Z which is selected from O, S, $NR^2$, cyclopropyl, $CO_2$, CHOH, a double or triple bond, $R^2$ is hydrogen and $C_1$–$C_4$ alkyl, B is 1,4-piperidinylene, 1,2,3,6-tetrahydro-1,4-pyridinylene, 1,4-piperazinylene or the corresponding cyclic compounds enlarged by one methylene group, with the linkage to A being via an N atom of B, and Ar is phenyl which is unsubstituted or substituted by $(C_{1-6})$ alkyl branched or unbranched, O—$(C_{1-8})$-alkyl branched or unbranched, F, Cl, Br, I, trifluoromethyl, $NR^2{}_2$, $CO_2R^2$, cyano or phenyl, or is tetratinyl, indanyl, fused aromatic systems.

2. A compound as defined in claim 1, where one of the two radicals X and Y is $CH_2$ and the other is $NR^1$, $R^1$ is hydrogen, $(C_{1-4})$ alkyl branched or unbranched, CO—$(C_{1-4})$-alkyl, $CO_2tBu$, COPh or a phenylalkyl $C_1$–$C_2$ radical which in turn can be substituted on the aromatic system by F, Cl, Br, I, $C_1$–$C_4$ alkyl, $C_1$–$C_4$ alkoxy, trifluoromethyl, hydroxyl or cyano, A is $(C_{2-5})$ alkylene branched or unbranched or $(C_{2-5})$ alkylene which comprises a group Z which is selected from CHOH, cyclopropyl, a double or a triple bond, B is 1,4-piperidinylene, 1,2,3,6-tetrahydro-1,4-pyridinylene, 1,4-piperazinylene or homopiperazinylene, where the linkage to A takes place via an N atom of B, and Ar is phenyl which is unsubstituted or substituted by $(C_{1-6})$ alkyl branched or unbranched, O—$(C_{1-6})$-alkyl branched or unbranched, F, Cl, Br, I, trifluoromethyl, $CO_2R^2$, $NR^2{}_2$, cyano or phenyl, or is tetralinyl, indanyl, fused aromatic systems.

3. A compound of the formula I as defined in claim 1, where one of the two radicals X and Y is $CH_2$ and the other is $NR^1$, $R^1$ is hydrogen, $(C_{1-2})$ alkyl, CO—$(C_{1-4})$-alkyl or a phenylalkyl $C_1$–$C_2$ radical, A is $(C_{2-3})$ alkyl, B is 1,4-piperidinylene, 1,4-piperidinylene or 1,2,3,6-tetrahydro-1,4-pyridinylene and Ar is pyrimidinyl, phenyl which is unsubstituted or substituted by $O(C_{1-2})$ alkyl in the ortho position, tetralinyl, indanyl or naphthyl which is unsubstituted or substituted by $(C_{1-4})$ alkyl or $O(C_{1-2})$ alkyl.

4. A compound of the formula I as claimed in claim 1, where Ar is naphthalene which is unsubstituted or substituted by $(C_{1-4})$ alkyl or $O(C_{1-4})$ alkyl, anthracene or 5- or 6-membered aromatic heterocycles having 1 or 2 heteroatoms which are selected, independently of one another, from O and N, which may be fused to other aromatic radicals, and their salts with physiologically tolerated acids.

5. A compound as defined in claim 2, where Ar is naphthalene which is unsubstituted or substituted by $(C_{1-4})$ alkyl or $O(C_{1-4})$ alkyl, or 5- or 6-membered aromatic heterocycles having 1 or 2 nitrogen atoms, which may be fused to other aromatic radicals.

6. A composition having a high affinity for $5\text{-HT}_{1B}$ and $5\text{-HT}_{1C}$ serotonin receptor which comprises a carrier or diluent and an effective amount of a compound as defined in claim 1.

7. A method of treating depression in a patient in need thereof which comprises administering to said patient an effective amount of a composition as defined in claim 6.

8. A method of selectively binding the receptors of $5\text{-HT}_{1B}$ or $5\text{-HT}_{1A}$ in a patient in need thereof which comprises administering to said patient an effective amount of a composition as defined in claim 6.

9. The method of claim 8, where the selective serotonin antagonism is supplemented by inhibition of serotonin reuptake.

* * * * *

UNITED STATES PATENT AND TRADEMARK OFFICE
CERTIFICATE OF CORRECTION

PATENT NO.    : 6,414,157 B1  
DATED         : July 2, 2002  
INVENTOR(S)   : Lubisch et al.

Page 1 of 1

It is certified that error appears in the above-identified patent and that said Letters Patent is hereby corrected as shown below:

Title page,
Insert -- [22] PCT Filed: Oct. 5, 1998
       [86] PCT No.: PCT/EP 98/06305
       § 371(c)(1),(2),(4) Date: Apr. 10, 2000
       [87] PCT Pub. No.: WO 99/21857
       PCT Pub. Date: May 6, 1999 --

Column 28,
Line 36, insert -- OH -- before "F".

Signed and Sealed this

Twenty-ninth Day of October, 2002

*Attest:*

*Attesting Officer*

JAMES E. ROGAN
*Director of the United States Patent and Trademark Office*